(12) United States Patent
Xue et al.

(10) Patent No.: US 12,104,191 B2
(45) Date of Patent: Oct. 1, 2024

(54) COFACTOR SELF-SUFFICIENT *Escherichia coli* AND CONSTRUCTION METHOD AND APPLICATION THEREOF

(71) Applicant: ZHEJIANG UNIVERSITY OF TECHNOLOGY, Zhejiang (CN)

(72) Inventors: Yaping Xue, Zhejiang (CN); Shuping Zou, Zhejiang (CN); Zhentao Jiang, Zhejiang (CN); Jianmiao Xu, Zhejiang (CN); Feng Cheng, Zhejiang (CN); Yuguo Zheng, Zhejiang (CN)

(73) Assignee: ZHEJIANG UNIVERSITY OF TECHNOLOGY, Zhejiang (CN)

( * ) Notice: Subject to any disclaimer, the term of this patent is extended or adjusted under 35 U.S.C. 154(b) by 0 days.

(21) Appl. No.: 17/823,853

(22) Filed: Aug. 31, 2022

(65) Prior Publication Data

US 2023/0084966 A1   Mar. 16, 2023

(30) Foreign Application Priority Data

Sep. 1, 2021   (CN) .......................... 202111022022.4

(51) Int. Cl.
| | |
|---|---|
| *C12P 13/00* | (2006.01) |
| *C07K 14/245* | (2006.01) |
| *C12N 1/21* | (2006.01) |
| *C12N 9/00* | (2006.01) |
| *C12N 9/04* | (2006.01) |
| *C12N 9/06* | (2006.01) |
| *C12N 9/10* | (2006.01) |
| *C12N 9/12* | (2006.01) |
| *C12N 15/10* | (2006.01) |
| *C12N 15/52* | (2006.01) |
| *C12N 15/70* | (2006.01) |

(52) U.S. Cl.
CPC .......... *C12P 13/001* (2013.01); *C07K 14/245* (2013.01); *C12N 9/0006* (2013.01); *C12N 9/0016* (2013.01); *C12N 9/1077* (2013.01); *C12N 9/1205* (2013.01); *C12N 9/1241* (2013.01); *C12N 9/93* (2013.01); *C12N 15/1082* (2013.01); *C12N 15/52* (2013.01); *C12N 15/70* (2013.01); *C12Y 101/01119* (2013.01); *C12Y 104/01002* (2013.01); *C12Y 204/02011* (2013.01); *C12Y 207/01086* (2013.01); *C12Y 207/07018* (2013.01); *C12Y 603/01005* (2013.01); *C12N 2800/101* (2013.01)

(58) Field of Classification Search
None
See application file for complete search history.

(56) References Cited

FOREIGN PATENT DOCUMENTS

CN           111621482 A  *  9/2020  .............. C12N 1/20

OTHER PUBLICATIONS

Uppada et al., Redesigning Cofactor Availability, Current Developments in Biotechnology and Bioengineering, Chapter 10, 2017. (Year: 2017).*

Yang et al., Improving the production of NAD+ via multi-strategy metabolic engineering in *Escherichia coli*, Metabolic Eng. 64, 2021. 122-33. (Year: 2021).*

* cited by examiner

*Primary Examiner* — Todd M Epstein
(74) *Attorney, Agent, or Firm* — MUNCY, GEISSLER, OLDS & LOWE, P.C.

(57) ABSTRACT

A cofactor self-sufficient *Escherichia coli* and its construction method and application in the synthesis of L-glufosinate are provided. The present invention expresses a NADH kinase and key enzymes of the cofactor synthesis pathway in *E. coli*, and knocks out the genes of enzymes that catabolizes cofactor, and with the addition of co-metabolic intermediates during cell incubation, the intracellular NADP(H) concentration is increased by at least 50% and the catalytic activity of glufosinate dehydrogenase by 2-fold, resulting in a significant increase in the spatiotemporal yield of the glufosinate synthesis reaction.

8 Claims, 11 Drawing Sheets
Specification includes a Sequence Listing.

SEQUENCE LISTING

```
Sequence total quantity: 16
SEQ ID NO: 1            moltype = DNA  length = 960
FEATURE                 Location/Qualifiers
source                  1..960
                        mol_type = genomic DNA
                        organism = Corynebacterium glutamicum
SEQUENCE: 1
atgacagcac ctaccaacgc aggggagctg cgtcgcgtcc ttctggtgcc acatactggt   60
cgttcttcga atatcgaatc cgcgatcctg gcagcgaaat tattagacga tgcggggatt  120
gatgtccgtg tccttattaa tgatgccgac gaccctattg ctgaacactc tgtattgggc  180
cgctttaccc acgttcgtca cgccgcagac gcggcagatg gagctgaact tgtccttgtt  240
ttgggggag acggcacctt cttgcgtgct gctgatatgg ctcacgcggt tgatctgccg  300
gttctgggaa tcaatttagg tcatgtgggc ttcctgcgg aatgggaaag tgatagtctg  360
gaggaagcat tgaagcgtgt gattgaccgt gactaccgca tcgaagatcg catgacactt  420
acagttgttg tcctggacgg gggtggtgaa gagattggac gtggctgggc acttaacgaa  480
gtgagcatcg aaaacctgaa tcgccgcggc gttttggatg caacgttgga ggtagacgct  540
cgtccagtag catccttcgg gtgcgacggg gtcttaatct ctactcccac aggctcgaca  600
gcttacgcct ttagcgctgg gggcccagtc ctgtggcctg aactggacgc gattttggtc  660
gtgcctaata acgcccatgc gttgtttacg aagcccttgg tcgtgtcgcc gaagagtaca  720
gtcgctgtcg aaagtaactc cgatactagc gcagctatgg cagtaatgga cggtttccgc  780
cccattccga tgccccctgg gagtcgcgta gaagtcactc gtggggaacg tccagtccgc  840
tgggtacgtc ttgactcctc accettcact gatcgtttgg tcagcaaact tcgcttacct  900
gtgacgggct ggcgtggccc gcaaaagcag gcagaaaata aagacccgcg cagcgcaggg  960

SEQ ID NO: 2            moltype = DNA  length = 876
FEATURE                 Location/Qualifiers
source                  1..876
                        mol_type = genomic DNA
                        organism = Escherichia coli
SEQUENCE: 2
atgaacaacc acttcaagtg cattggtatt gtcgggcacc ctcgccatcc tacggctctt   60
acaacacacg aaatgttata tcgctggttg tgtaccaagg gctacgaagt cattgttgaa  120
cagcagattg cacatgaact gcaacttaaa aatgtcagca ctggaaccTt agctgaaatt  180
ggacaactgg cagatttggc ggtcgtcgta gggggggacg gaaatatgtt gggtgctgcc  240
cgcacttTgg cacgctatga tattaaggta atcgggatta accgtggtaa ccttggattc  300
ctgactgatc tggacccaga caacgcacag cagcaacttg ctgatgtgct ggaaggacac  360
tatatttccg agaagcgttt cctTctggag gcgcaagtat gccagcaaga ctgccagaaa  420
cgtatttcaa cggccattaa tgaagtagtt ctgcaccctg ggaaagtagc acatatgatc  480
```

```
gagttcgagg tgtacatcga cgagatcttc gcattctcgc agcgttcgga cggtttaatc    540
atcagtacac caactggctc aaccgcgtat tccttatcgg ccggtggccc gattttgact    600
ccgtcattgg atgctattac tctggtgccc atgtttcccc atacattatc tgcccgtcca    660
ttagtaatta acagttcatc aacaatccgt ctgcgcttct ctcaccgccg taatgacctg    720
gagatttcct gcgactctca aatcgcactg cctatccaag agggtgaaga tgttcttatt    780
cgtcgttgcg attaccactt aaatcttatt catccgaaag actattccta ctttaacaca    840
cttagtacga agttaggctg gtccaaaaaa ttattt                              876

SEQ ID NO: 3            moltype = DNA   length = 1722
FEATURE                 Location/Qualifiers
source                  1..1722
                        mol_type = genomic DNA
                        organism = Methanocaldococcus jannaschii
SEQUENCE: 3
atggtcatca tggaagggtt taaaatcgct atgaaggtga ttgacgaaat cgataaaaag    60
attaagccat taattgggtg ggaaaaggcc gatgaagtcg ttaaaattgg ggctgacggt    120
actcctacaa aacgcattga tgtaattgca gaaaacatgg cgattaacat cttggagaaa    180
ttctctggtg gtatcttaat ttctgaagaa atcggattga aagtggtagg agatgaatta    240
gagtatatct ttattcttga tcctatcgac ggtacgtata acgcattgaa atcaattccc    300
atctattcta ccagcatcgc cgtcgcgaag atcaagggtg aagataaaaa gttaattcgt    360
gagaatatca acaatattga ttggatcaaa tcttttatcg ccaataaata tactattaat    420
gacctttatg ttggcatcgt aaagaatctg gctactggcg ccttttacta tgcaattaag    480
ggcgaaggct ccttcttaga aaagacgggg gaaaaaatta agattgaaac taagaatatt    540
aaagacttaa aggaggcgtc ggttggtttg tttgtatatg gcttgagtaa tgatttattg    600
gaattcctta agaacgtaaa agtccgccgt gttcgtttgt ttggttcaat ggcattagag    660
atgtgttacg tggtatcggg ggcgcttgac gcatatatta acgtaaatga gaacagtcgt    720
ctttgtgata tcgcgggtgc gtatgtaatt tgtcgcgaag ggaacgcaat cgtaaccaat    780
aagaacggaa aaccgttaaa tatgaaattg cacctgatgg aacgtacttc actgatcgtc    840
agcaacaaat accttcataa aaaacttatt gctctttttg gaaaccgttg gatcattaag    900
ccagtcaaat ttggaatcgt ggtccgcgag gataaggagg aggcaattaa ccttgccatc    960
gaaatttgta agtacttgaa agataaaaac atcccattct gcgtggaaga tttcctgcgc    1020
gaacgcgttg ggggtgataa attcgatatc agtgccattt cacacattat tgccatcggg    1080
ggagacggaa ctattttacg tgctagtcgc cttgtgaatg tgagacaat tccaattatt    1140
gcagttaaca tgggaaagt cggttttctt gccgagtttt gcaaggatga ggtcttcgaa    1200
atcattgata aggtgattta cggggagtac gaaattgaaa acgctcgaa gttatcctgc    1260
aagattatca aggacaaccg tgttatcaaa acaccatccg ccttgaacga aatggtggtt    1320
atcactaaga acccagcgaa gatcctgaaa ttcgatgtct acgtaaacga cacgcttgta    1380
gagaacgtgc gcgctgacgg tatcatcgta agcacggcta ctggatcgac agcctattct    1440
ttgtccgcgg gagggccaat cgttgaacca aatgtagatt gcttcattat ctcgcctatt    1500
tgtccattta aactgtcaag ccgtccgctt gttatttcag cgtcgaatcg cattaagtta    1560
aagcttaagc tggaaaaacc cgctcttttta gtcatcgacg ggagcgtaga gtacgaaatt    1620
aacaaagatg atgaactgat cttttgagaaa tccgatagtt acgcatactt cgtgaagggc    1680
caatcgtttt acaacaagtt aagtcgctgt cttggtatta aa                       1722

SEQ ID NO: 4            moltype = DNA   length = 783
FEATURE                 Location/Qualifiers
source                  1..783
                        mol_type = genomic DNA
                        organism = Entamoeba histolytica
SEQUENCE: 4
atgaccacat tacagattga tcatattcgt gctaaattcc atattgacga ctacaaccaa    60
aaggctcctg acgtggcccg ccagtttgaa cgtattcatg atgaagtcaa tccaaacgtc    120
gtcatgacgt tcggggagaa tggcaccttc ctgaaagcct ttcacgaaaa ttatcatctt    180
caacttccct accttggaat taattgtggg aacgtgggtt atctgatcaa cccaatccaa    240
gaagttatgg acagcatcga gcaaaacaag cccttaaatt gctactctta tccttgcctg    300
aaggttgatg cctcaaacgg agcacgcag ctgtcgaccc aacttgcatt caacgcgct    360
tggattgaac gccttaacgg acaatgctgc tggttcgagg tcatcatcaa cggggttgta    420
cgtatcccaa aattgtgttg tgacggaatt gtggtatgta cccctgccgg cagcacgggc    480
tactccaagt ccattggcgt catgccaatt cctccaaatg catcgaactgt cgggtttgtt    540
cctaataacg cgagctaccc tttgggcatt cgcccttat atctgccgtt agacacagag    600
gtaattgtta aaaatatcca gccaaacgt cgtaaaacac gcggattta tgatgggtc    660
gagctgaacg aaatcactga attgaagatc aaggctatcg agaacggctg ccgcgttatc    720
tacgctcatg aggagaacct gaacaaaacc tacattaata aagtcacaaa ggatttcttt    780
gaa                                                                   783

SEQ ID NO: 5            moltype = DNA   length = 1242
FEATURE                 Location/Qualifiers
source                  1..1242
                        mol_type = genomic DNA
                        organism = Saccharomyces cerevisiae
SEQUENCE: 5
atgttcgtcc gtaaaaact taataagcca gttaatggt atcgctttta ttccacgctt    60
gattcacatt cgctgaaatt acagagtggg tctaaattcg ttaagattaa acctgtcaac    120
aacctgccgt cctagtagttc agcggatttc gtcaactcca attacagtcg                180
ttgatctggc agaatccttt acagaatgtg tatattacca agaagccgtg gactccatca    240
actcgcgagg ctatggtgga gttcattact caccttcacg agtcctaccc cgaggtaaac    300
gttattgtcc agcctgacgt tgccgaagaa atcagtcaag actttaaatc tcctctggag    360
aacgacccta atcgccgca tattctgtat acgggtcccg aacaggacat cgtcaatcgc    420
actgacttgt tggtgacgtt agggggtgac gggactatcg tgcacgggt ctccatgttt    480
```

```
ggtaatacgc aagtgcctcc cgttcttgca ttcgcgcttg gaaccctgg gttcttgtcc    540
cccttgatt ttaaagagca taagaaagtt tttcaagagg ttatctcttc gcgtgcaaag    600
tgtctgcatc gtacccgttt ggaatgtcat cttaagaaaa aagattcgaa ttccagtatt   660
gtaacccacg ccatgaatga tattttctta caccgcggca attcaccca tttaaccaat   720
ctggacatct ttattgatgg agagttttg actcgcacca cggctgacgg tgtcgcttta   780
gcaacgccca ctggatctac agcgtactca ttatctgctg gcggcagcat tgttagccca   840
ctggtccctg ctatcctgat gactccgatc tgcctcata gtctgtcttt cgcccttg     900
attttgcccc actcaagcca tatccgcatc aaaatcggat caaaacttaa ccagaaacct   960
gtcaactccg tagtaaagtt atcggtggat gggattccac agcaggacct tgacgttgga  1020
gacgaaattt atgtcatcaa tgaggtgggc acaatttata ttgatgggac tcaattgcca  1080
actaccgcta agacagaaaa cgatttaat aattcaaaga aaccaaaacg tagtggtatt   1140
tattgtgtgg ctaagacaga gaacgattgg atccgcggga tcaatgagtt gttaggatt   1200
aactcatcct ttcgcttaac gaagcgtcaa accgataatg at                     1242

SEQ ID NO: 6              moltype = DNA    length = 789
FEATURE                   Location/Qualifiers
source                    1..789
                          mol_type = other DNA
                          organism = unidentified
SEQUENCE: 6
atgggttata attctctgaa aggcaaagtc gcgattgtta ctggtggtag catgggcatt     60
ggcgaagcga tcatccgtcg ctatgcagaa gaaggcgatc gcgttgttat caactatcgt    120
agccatccgg aggaagccaa aaagatcgcc gaagatatta acaggcagg tggtgaagcc    180
ctgaccgtcc agggtgacgt ttctaaagag gaagacatga tcaacctggt gaaacagact    240
gttgatcact tcggtcagct ggacgtcttt gtgaacaacg ctggcgttga gatgccttct    300
ccgtcccacg aaatgtccct ggaagactga cagaaagtga tcgatgttaa tctgacgggt    360
gcgttcctgg cgctcgtga agctctgaaa tacttcgttg aacataacgt gaaaggcaac    420
attatcaata tgtctagcgt ccacgaaatc atcccgtggc ctactttcgt acattacgct    480
gcttctaagg gtggcgttaa actgatgacc cagactctgg ctatggaata tgcaccgaaa    540
ggtatccgca ttaacgctat cggtccaggc gcgataaaca ctccaattaa tgcagaaaaa    600
ttcgaggatc cgaaacagcg tgcagacgtg gaaagcatga tcccgatggg caacatcggc    660
aagccagagg agatttccgc tgtgcggca tggctggctt ctgacgaagc gtcttacgtt    720
accggcatca ccctgttcgc agatggtggc atgaccctgt accgagctt tcaggctggc    780
cgtggttga                                                           789

SEQ ID NO: 7              moltype = DNA    length = 1338
FEATURE                   Location/Qualifiers
source                    1..1338
                          mol_type = other DNA
                          organism = unidentified
SEQUENCE: 7
atgattgaga gcgtcgagtc tttcttggcc cgccttaaaa agcgcgaccc tgaccagccg     60
gagtttcatc aggcagttga ggaagtctta cgctcattat ggccgttcct ggaagctaac    120
ccccgttatt tgactagcgg cattcttgaa cgtatttgcg agccggaacg tgccatcgtt    180
ttccgtgtga gctgggtaga cgaccaagga aaggtgcaag tgaaccgtgg cttccgcatc    240
cagatgaact cagctatcgg cccatataaa ggcgggttgc gttttcatcc aagcgttaat    300
ttgggtgtct taaaattctt agcgttcgag caaacattta aaaacagctt aacatcgtta    360
cccatgggtg gaggaaaggg tggtagtgac ttcgacccaa aggggaagag cgatgcggaa    420
gtcatgcgtt tctgccaggc attcatgtca gagctttacc gtcacatcgg ggcggacgtc    480
gatgtgccag cggagatat tggcgtgggt gcgcgcgaga ttggattttt attcggtcag    540
tataaagtc tgtctaacca gttcacctcg gtacttacgg gtaagggacc gtcatatgcg    600
ggcagtttga ttcgcccaga agctaccgga tttggttgtg tttatttgc cgaagaaatg    660
cttaagcgcc gtggagaaac cgtggaaggc aagcgtgttg ccattagtgg ctctgggaac    720
gtagcgcagt atgcggcccg caaggtgatg atcttggcg aaaagtcat ttctttatca    780
gacagcgagg gcacattata ctgcgaatcc ggtttgactg aagctcaatg gcaagcagtg    840
ttggaactga agaatgtaca acgtggccgt atttcagaat tagccggacg ctttggtctt    900
gaatttttag cgggccaacg ccctggggt ttatctgcg atatcgccct tccttgcgcg    960
acgcagaacg agcttgacgc cgaagctgcg cgtgctttac ttcgtaatgg atgcacgtgc   1020
gtcgctgaag gggcgaacat gccgacaacc cttgaggcgg ttgatctgtt tatcgaagcg   1080
ggtattctgt tcgctccagg taaagcctcg aatgctggcg tgcagt gtcggtgttta     1140
gagatgtcgc aaaacgcaat gcgttattg tggacagggg gcgaggttga ctcaaaattg   1200
catgctatca tgcagagcat ccatcatgct tgcgtacatt acggtgaaga gaacggtcag   1260
gtaaaactacg taaaggggc gaatattgct ggattcgtga aggttgctga tgcaatgctg   1320
gcacaggggg tcgtctaa                                                 1338

SEQ ID NO: 8              moltype = DNA    length = 828
FEATURE                   Location/Qualifiers
source                    1..828
                          mol_type = other DNA
                          organism = unidentified
SEQUENCE: 8
atgacattgc aacaacaaat aataaaggcg ctgggcgcaa aaccgcagat taatgccgaa     60
gaggaaattc gtcgtagtgt cgatttctgt aaaagctacc tgcgaactta ccgttcatt    120
aaatcactgg tgctcgggat cagcggcggt caggactccg cgcttgccgg aaagctgtgc    180
cagatggcga ttaatgagct gcgcaggaa accggcaacg aatcactgca atttattgcc    240
gtacgcctgc cctatggtgt tcaggccgac gaacaagatt gccaggatgc cattgccttt    300
attcaaccgg atcgcgtatt aaccgttaat atcaaggcgc ggtattggc tagcgagcag    360
gcattgcggg aagcaggcat tgaactgagc gattttgtcc gtggcaatga aaagcgcgt    420
gagcggatga aagcacaata tagcattgcg ggtatgacca gcggtgtcgt ggtgggcacc    480
```

```
gatcatgcag cagaagccat taccggattc ttcactaaat atggtgacgg cggtacggat   540
attaatccgc tgtatcgtct caacaaacgt cagggtaaac agttactggc ggcattaggt   600
tgcccggaac acctttataa gaaagcgcca acggccgatc tggaagatga tcgcccttct   660
ctgccagatg aagtggcact cggcgtgacc tatgacaata tcgacgacta tctggaaggg   720
aaaaacgtac ctcaacaggt cgccagaaca atagagaact ggtatctgaa aaccgaacat   780
aaacgccgtc cgccaattac cgttttcgat gatttctgga aaaagtaa                828

SEQ ID NO: 9              moltype = DNA  length = 642
FEATURE                   Location/Qualifiers
source                    1..642
                          mol_type = other DNA
                          organism = unidentified
SEQUENCE: 9
atgaaatctt tacaggctct gtttggcggc acctttgatc cggtgcacta tggtcatcta    60
aaacccgtgg aaacgctggc gaatttgatt ggtctgacgc gggtcacaat catccctaat   120
aatgttcctc cgcatcgtcc ccagccggaa gcgaacagcg tgcagcgtaa acacatgctt   180
gaactggcga ttgccgacaa gccattattt actcttgatg aacgcgagct aaagcgcaat   240
gcccccctctt acactgcgca aacactgaaa gagtggcggc aggaacaagg accggacgtg   300
ccgctggcgt ttattattgg tcaggattca ttgctgacct ttccgacctg gtacgaatac   360
gaaacgatac tcgacaatgc acatttgatc gtctgtcggc gtccaggtta cccacttgaa   420
atggcgcaac cgcaatacca gcaatggctg aagatcatt tgcacataa cccggaagat   480
cttcaccttc agcctgccgg taaaatttat ctggctgaaa ccgcgtggtt taacatctcg   540
gcgaccatca tccgcgaacg tttgcaaaac ggtgaatcgt gtgaggattt attgccgaa   600
ccggtattga cttacattaa ccaacaaggc ttgtatcgct ga                      642

SEQ ID NO: 10             moltype = DNA  length = 1203
FEATURE                   Location/Qualifiers
source                    1..1203
                          mol_type = other DNA
                          organism = unidentified
SEQUENCE: 10
atgacacaat tcgcttctcc tgttctgcac tcgttgctgg atacagatgc ttataagttg    60
catatgcagc aagccgtgtt tcatcattat tacgatgtgc atgtcgcggc ggagtttcgt   120
tgccgaggtg acgatctgct gggtatttat gccgatgcta ttcgtgaaca gattcaggcg   180
atgcagcacc tgcgcctgca ggatgatgaa tatcagtggc tttctgccct gccttttcttt  240
aaggccgact atcttaactg gttacgcgag ttccgcttta acccggaaca agtcaccgtg   300
tccaacgata atggcaagct ggatattcgt ttaagcggcc cgtggcgtga agtcatcctc   360
tgggaagttc ctttgctggc ggttatcagt gaaatgtac atcgctatcg ctcaccgcag   420
gccgacgttg cgcaagccct cgacacgctg gaaagcaaat tagtcgactt ctcggcgtta   480
accgccggtc ttgatatgtc gcgcttccat ctgatggatt ttggcacccg tcgccgtttt   540
tctcgcgaag tacaagaaac catcgttaag cgtctgcaac aggaatcctg gtttgtgggc   600
accagcaact acgatctggc gcgtcggctt tccctcacgc cgatgggaac acaggcacac   660
gaatggttcc aggcacatca gcaaatcagc ccggatctgg ccaacagcca gcgagctgca   720
cttgctgcct ggctgaagaa gtatcccgac caacttggca ttgcattaac cgactgcatc   780
actatggatg ctttcctgcg tgatttcggt gtcgagttcg ctagtcggta tcaaggcctg   840
cgtcatgact ctggcgaccc ggttaatgg ggtgaaaaag ccattgcaca ttatgaaaag   900
ctgggaattg atccacagag taaaaacgctg gttttctca acaatctgga tttacgcaaa   960
gcggttgagc tataccgcca cttctcttcc cgcgtgcaat taagttttgg tattgggact  1020
cgcctgacct gcgatatccc ccaggtaaaa cccctgaata ttgtgattaa gttggtagag  1080
tgtaacggta accggtggc gaaactttct gacagccctg gcaaaactat ctgccacgat  1140
aaagcgtttg ttcgggcgct cgcaaaagcg ttcgaccttc cgcatattaa aaaagccagt  1200
taa                                                                1203

SEQ ID NO: 11             moltype = DNA  length = 20
FEATURE                   Location/Qualifiers
source                    1..20
                          mol_type = other DNA
                          organism = unidentified
SEQUENCE: 11
acaaaaatta tggttgccga                                                20

SEQ ID NO: 12             moltype = DNA  length = 120
FEATURE                   Location/Qualifiers
source                    1..120
                          mol_type = other DNA
                          organism = unidentified
SEQUENCE: 12
cagtgagaaa tgtaaaaacc atgttaaaca tgccagtgat gcaaaggtag tgcaagagct    60
tgatacactg accgcctgac gcactaagga acagccaaaa tgaccgaact taaaaacgat   120

SEQ ID NO: 13             moltype = DNA  length = 20
FEATURE                   Location/Qualifiers
source                    1..20
                          mol_type = other DNA
                          organism = unidentified
SEQUENCE: 13
atccggaaaa cggctgcccg                                                20

SEQ ID NO: 14             moltype = DNA  length = 120
```

```
FEATURE             Location/Qualifiers
source              1..120
                    mol_type = other DNA
                    organism = unidentified
SEQUENCE: 14
tcacttctat tctggtcaca ggtttccacc tgacagaccc gcaattttca ggacaattca    60
gggaattacg cggtcaagcg ccatttgtgt cattttttaa atgacaagcg cttgatttgc   120

SEQ ID NO: 15       moltype = DNA   length = 20
FEATURE             Location/Qualifiers
source              1..20
                    mol_type = other DNA
                    organism = unidentified
SEQUENCE: 15
gggctgcacg ctacagcagg                                                20

SEQ ID NO: 16       moltype = DNA   length = 120
FEATURE             Location/Qualifiers
source              1..120
                    mol_type = other DNA
                    organism = unidentified
SEQUENCE: 16
aaaactctcc gacgcgctta gcgtgttcga cgacttataa tgaggaatac ggagggagat    60
ccgcgatgaa acggctcaaa ggcgaggtat aaaataagtt ttttgatgag ttgaaaacct   120
```

COFACTOR SELF-SUFFICIENT *Escherichia coli* AND CONSTRUCTION METHOD AND APPLICATION THEREOF

CROSS-REFERENCE TO RELATED APPLICATIONS

This U.S. patent application claims the priority of Application No. CN202111022022.4 filed in China on Sep. 1, 2021, the entire contents of which are hereby incorporated by reference.

The instant application contains a Sequence Listing which has been submitted electronically in the ASCII text file and is hereby incorporated by reference in its entirety. The ASCII text file is a sequence listing entitled "2022-08-31-SEQ" created on Aug. 31, 2022 and having a size of 25,555 bytes in compliance of 37 CFR 1.821.

TECHNICAL FIELD

The invention relates to a cofactor self-sufficient *Escherichia coli*(hereinafter, *E. coli*) constructed by genetic engineering technology and fermentation engineering technology, as well as the constructing method and its application in catalytic synthesis of glufosinate-ammonium.

BACKGROUND

Glufosinate-ammonium(hereinafter, glufosinate) is the world's second largest kind of genetically modified crop tolerated herbicide. It is developed and produced by Heaster (after several merges, it belongs to Bayer Company). The chemical name is 4-[hydroxyl (methyl) phosphoryl]-DL-homoalanine, also known as the Glufosinate ammonium, Basta, Buster, etc., which belongs to the phosphonic acids, which is a glutamine-synthetase inhibitor, Non-selective (extinguishing) touch-type herbicide.

At present, the three major herbicide varieties in the world are glyphosate, glufosinate, and blossoms. Compared with glyphosate and blossoms, glufosinate has excellent weeding performance and smaller medicine and side effects. With the rapid development of glufosinate-resistant transgenic crops, the market demand in the glufosinate will be huge in the future, and the prospects are very broad.

There are two types of optical heterogeneity, which are D- and L-isomers. However, only the L-type has physiological activity, and it is easy to break down in the soil. It has less toxicity to humans and animals, a broad weeding spectrum, and small destructive impact on the environment.

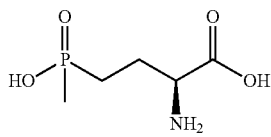

At present, the glufosinate sold on the market is generally a racemic mixture. If glufosinate products can be used as optically pure isomers of L-configuration, the amount of glufosinate used can be reduced by 50%, which is of great importance to improve atomic economy, reduce costs and alleviate environmental pressure. The currently reported methods for producing L-glufosinate mainly include chemical synthesis, including disassembly of racemic glufosinate, chiral raw material method, chiral cofactor method and asymmetric catalytic method, but there are problems such as racemization and reuse of D-glufosinate is not easy, lengthy synthesis steps, the reaction requires ultra-low temperature, low product ee value, low yield, and expensive chiral disassembly reagents. In contrast, the biosynthesis method has the advantages of strict stereoselectivity, mild reaction conditions and easy product separation and purification, so it is of great industrial value and significant social benefits to explore the feasibility of biological method to produce L-glufosinate.

Using D, L-glufosinates as the raw material, in which D-glufosinate is catalyzed by D-amino acid oxidase to obtain L-glufosinate precursor 2-carbonyl-4-[hydroxy (methyl)phosphono]butanoic acid (PPO), and then catalyzed by amino acid dehydrogenase or transaminase to obtain L-glufosinate, which not only solves the problem of racemization but also saved cost.

NAD(H) and NADP(H) are key cofactors that play important roles in all organisms and have a clear division of labor. Many redox processes require the participation of NAD(H) and NADP(H), for example, the asymmetric reductive amination of PPO catalyzed by amino acid dehydrogenase requires NADPH to provide reducing power. However, the deficiency of intracellular endogenous NAD(P)(H) usually becomes a limiting factor for the catalytic efficiency of such cofactor-dependent oxidoreductases. Therefore, it is crucial to regulate the intracellular NAD(H) and NADP(H) concentrations.

*E. coli* is capable of synthesizing NAD(P) cofactors on its own, including a de novo synthetic pathway with L-aspartate as the starting substrate and a remedial pathway with nicotinic acid as the substrate, with multiple enzymes involved in regulating each step of this metabolic pathway. Among them, the more critical ones include: NAD synthase encoded by the nadE gene, nicotinic acid adenyltransferase encoded by the nadD gene, and nicotinic acid phosphate ribosyltransferase encoded by the pncB gene, etc. The amount of intracellular NAD(P) synthesis is mainly controlled by these enzymes. In addition, cofactor catabolic pathways exist, mainly including mazG, mudC, nadR and other gene-regulated cofactor catabolism.

In addition, a key enzyme that regulates intracellular NAD(H) and NADP(H) concentrations is NAD(H) kinase, which catalyzes the phosphorylation of NAD(H) with ATP or inorganic polyphosphate [poly(P)] as phosphoryl donor to generate NADP(H). NAD(H) kinase (EC2.7.1.23; NADK) can only specifically bind $NAD^+$ to phosphorylation to $NADP^+$, which is the final step in the $NADP^+$ biosynthetic pathway. Depending on the phosphoryl receptor, NADH kinases are classified as poly(P)/ATP-NADH kinases and ATP-NADH kinases. Unlike the specificity of NAD(H) kinases, NADH kinase (EC2.7.1.86; NADHK) can catalyze not only NAD but also phosphorylation of NADH to form NADPH, but preferentially using NADH as a substrate.

Since L-aspartate, quinolinic acid, nicotinic acid and nicotinamide are precursors or intermediates in the cofactor synthesis pathway, after lifting the rate-limiting steps regulated by key genes, the intracellular cofactor concentration can be further increased by the addition of these compounds.

In previous work, the applicant constructed an engineered strain of *E. coli* containing a glufosinate dehydrogenase and glucose dehydrogenase, which was able to catalyze the asymmetric amination reduction of 2-carbonyl-4-(hydroxymethylphosphinyl)-butyrate to L-glufosinate in the presence of NADPH, and regenerate the cofactors via glucose dehydrogenase, but the low concentration of endogenous cellular NADP(H) limited the glufosinate dehydrogenase catalytic efficiency, limiting its industrial application.

SUMMARY OF THE INVENTION

The purpose of the present invention is to construct cofactor self-sufficient *E. coli* and use the engineered bacteria to synthesize glufosinate with high efficiency catalysis to solve the current problem of insufficient endogenous cofactor concentration in *E. coli*.

The technical solution used in the present invention is.

A cofactor self-sufficient *E. coli*, obtained by constructing methods as follows.

(1) constructing expression vectors, transforming NADH kinase gene, glucose dehydrogenase gene, glufosinate dehydrogenase gene and genes of NADP cofactor synthesis pathway into *E. coli* BL21 (DE3), screening the correct transformants, and obtaining glufosinate dehydrogenase-glucose dehydrogenase-NADH kinase co-expressing gene engineering bacteria; said NADH kinase gene sequence is one of SEQ ID No. 1 to 5, said glucose dehydrogenase gene sequence is as shown in SEQ ID No. 6, said glufosinate dehydrogenase gene sequence is as shown in SEQ ID NO. 7, and said NADP cofactor synthesis pathway gene sequence is as shown in one of SEQ ID No. 8 to 10.

(2) Knocking out of any one or a combination of mazG, mudC, nadR in the genome of the co-expressing gene engineering bacterium to obtain a cofactor self-sufficient recombinant *E. coli*. Said recombinant *E. coli* expresses both exogenous glufosinate dehydrogenase, glucose dehydrogenase, NADH kinase and enzymes of the cofactor synthesis pathway and the cofactor catabolic genes are knocked out on the basis of the host *E. coli*.

Preferably, the sequence of said NADH kinase gene in step (1) is as shown in SEQ ID No. 3, and the sequence of said NADP cofactor synthesis pathway gene is as shown in SEQ ID No. 8.

Preferably, the mazG and nadR genes are knocked out in step (2).

Said NADH kinase is derived from *Corynebacterium glutamicum* (CgNadK) (accession no. NC_003450.3), *Escherichia coli* (EcNadK) (accession no. NC_000913.3), *Methanocaldococcus jannaschii* (MjNadK) (accession no. NC_000009.12), *Entamoeba histolytica* (EhNadK) (accession no. NW_001914860.1), *Saccharomyces cerevisiae* (ScNadK) (accession no. NC_001148.4).

Said enzymes of the cofactor synthesis pathway include *E. coli* endogenous NAD synthase (nadE), nicotinic acid adenyltransferase (nadD), and nicotinic acid phosphoribosyltransferase (pncB).

The NCBI accession number of said knockout gene nadR is ACT46046.1, the NCBI accession number of mazG is ACT44443.1, and the NCBI accession number of nudC is ACT45665.1.

The present invention also relates to a method for constructing said cofactor self-sufficient *E. coli*, said method comprising:

(1) constructing expression vectors, transforming NADH kinase gene, glucose dehydrogenase gene, glufosinate dehydrogenase gene and genes of NADP cofactor synthesis pathway into *E. coli* BL21 (DE3), screening the correct transformants, and obtaining glufosinate dehydrogenase-glucose dehydrogenase-NADH kinase co-expressing gene engineering bacteria; said NADH kinase gene sequence is as one of SEQ ID No. 1 to 5, said glucose dehydrogenase gene sequence is as shown in SEQ ID No. 6, said glufosinate dehydrogenase gene sequence is as shown in SEQ ID NO. 7, and said NADP cofactor synthesis pathway gene sequence is as shown in one of SEQ ID No. 8 to 10.

(2) Knocking out of any one or a combination of mazG, mudC, nadR in the genome of the co-expressing gene-engineering bacterium to obtain said cofactor self-sufficient *E. coli*.

Preferably, the sequence of said NADH kinase gene in step (1) is as shown in SEQ ID No. 3 and the gene sequence of said NADP cofactor synthesis pathway is as shown in SEQ ID No. 8; the mazG and nadR genes are knocked out in step (2).

The intracellular cofactor concentration can be increased by inoculating the recombinant *E. coli* into a medium containing 5 to 40 mg/L cofactor synthesis precursor. Said cofactor synthesis precursor is one of the following: L-aspartic acid, quinolinic acid, nicotinic acid, nicotinamide.

The invention also relates to the application of said cofactor self-sufficient *E. coli* in the preparation of L-glufosinate by microbial fermentation.

Specifically, said application is: using the wet bacteria obtained by fermentation culture of said cofactor self-sufficient *E. coli* or the enzyme solution extracted by ultrasonic crushing of said wet bacteria as the catalyst, using 2-carbonyl-4-(hydroxymethylphosphinyl)-butyric acid as the substrate, adding ammonium sulfate and glucose, using pH 7.5 buffer as the reaction medium to constitute the reaction system, and reacting at 35° C.~40° C., 500~600 rpm; after the reaction, the reaction solution is separated and purified to obtain L-glufosinate.

In said reaction system, the amount of catalyst is 10~50 g/L by weight, the initial concentration of substrate is 10~500 mM, the addition of glucose is 12~750 mM, and the addition of ammonium sulfate is 50 mM~1.5M.

Preferably, in said reaction system, the amount of catalyst is 15 g/L by total weight of wet bacteria, the initial concentration of substrate is 200 mM, the amount of glucose addition is 250 mM, and the amount of ammonium sulfate addition is 300 mM.

The beneficial effects of the present invention are mainly reflected in that the present invention expresses the genes of NADH kinase and cofactor synthesis pathway in *E. coli* and knocks out the genes of cofactor catabolism, and increases the intracellular NADP(H) concentration by at least 50% during the cell culture process by the addition of combined metabolic intermediates and the conversion of intracellular NAD(H) to NADP(H) by NADH kinase, and the catalytic activity by 2-fold. During the asymmetric reductive amination of 2-carbonyl-4-(hydroxymethylphosphinyl)-butyric acid, NADH kinase continued to convert intracellular NAD(H) to NADP(H), slowing down the decrease in glufosinate dehydrogenase activity due to the short half-life of NADP(H), shortening the course of the asymmetric reductive amination reaction by at least 5 h, and significantly improving the spatiotemporal yield of the reaction.

DETAILED DESCRIPTION OF THE EMBODIMENTS

Figure 1:
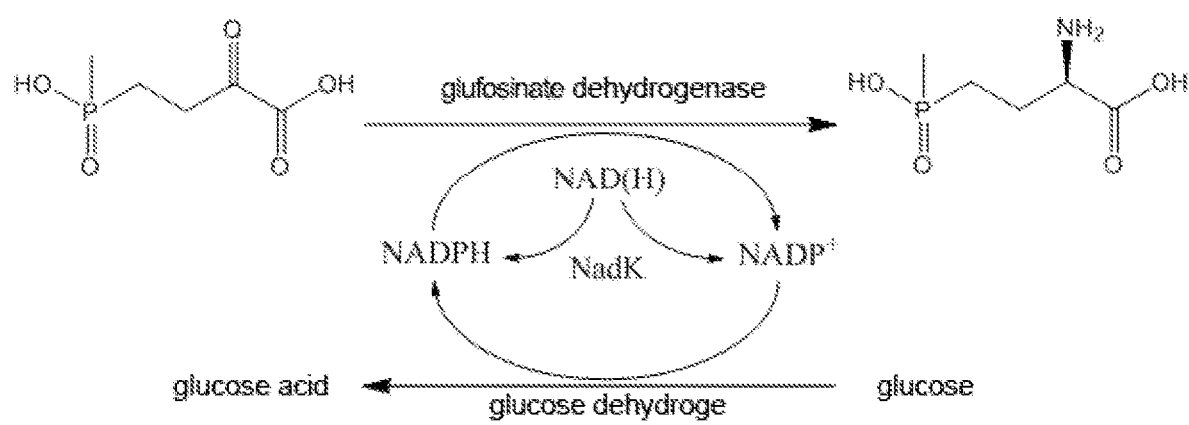
FIG. 1 shows the reaction equation of NAD(H) kinase catalyzing the synthesis of NADP(H) and glufosinate dehydrogenase coupled with glucose dehydrogenase for cofactor regeneration to efficiently catalyze the synthesis of L-glufosinate from 2-carbonyl-4-(hydroxymethylphosphinyl)-butyrate.

The present invention is further described below in connection with specific embodiments, but the scope of protection of the present invention is not limited to this.

The experimental methods in the present invention are conventional if not specifically stated, and the gene cloning operations can be specifically described in the Guide to Molecular Cloning Experiments, edited by J. Sambrook et al.

Reagents used in upstream genetic engineering operations: the one-step cloning kits used in the embodiments were purchased from Vazyme, Nanjing Novozymes Biotechnology Co. The DNA marker, FastPfu, low molecular weight standard protein, agarose electrophoresis reagent, primer synthesis and gene sequencing were done by Hangzhou Zixi Biotechnology Co. The above reagents are used in accordance with the product specifications.

Reagents used in the downstream catalytic process: 2-carbonyl-4-(hydroxymethylphosphinyl)-butyric acid (PPO), D,L-glufosinate, L-glufosinate (L-PPT) standards were purchased from Sigma-Aldrich; other common reagents were purchased from Sinopharm Chemical Reagent Co., Ltd.

Embodiment 1: Knockout of Cofactor Catabolic Gene

The mudC, mazG and nadR on Escherichia coli BL21 (DE3) were subjected to single or double knockdown, wherein the plasmid used for knockdown in this invention was pCasRed with pCRISPR-gDNA (sgRNA), which was introduced into Escherichia coli BL21 (DE3) together with the homologous arm (donor). Cas9/sgRNA induced a double-stranded break in the host at the target gene locus, and recombinase Red integrated the donor into the target gene to achieve gene knockdown, which was verified by sequencing. mudC sgRNA, mudC donor, mazG sgRNA, mazG donor, nadR sgRNA, nadR donor are respectively as shown in the sequential list SEQ ID NO 16-SEQ ID NO 21. The changes in intracellular cofactor concentrations of the strains obtained with different knockout combinations are shown in Table 1.

TABLE 1

| | Changes in cofactor concentration after knockdown |
|---|---|
| Strain | Concentration (μmol/g) of NADP (H) cofactor |
| E. coli BL21(DE3) | 21.4 |
| E. coli BL21(DE3) ΔmudC | 24.7 |
| E. coli BL21(DE3) ΔmazG | 22.8 |
| E. coli BL21(DE3) ΔnadR | 31.5 |
| E. coli BL21(DE3) ΔmudC ΔnadR | 29.6 |
| E. coli BL21(DE3) ΔmazG ΔnadR | 33.4 |
| E. coli BL21(DE3) ΔmazG ΔmudC ΔnadR | 32.1 |

As seen in Table 1, E. coli BL21(DE3) ΔmazG ΔnadR worked best and was named E. coli BL21(DE3) MN.

Embodiment 2: Construction of E. coli Containing NADH Kinase

In this Embodiment, five NADH kinase sequences which were reported in the literature were selected in the NCBI database from *Corynebacterium glutamicum* (CgNadK) (accession no. NC_003450.3), *Escherichia coli* (EcNadK) (accession no. NC_000913.3), *Methanocaldococcus jannaschii* (MjNadK) (accession no. NC_000009.12), *Entamoeba histolytica* (EhNadK) (accession no. NW_001914860.1), *Saccharomyces cerevisiae* (ScNadK) (accession number NC_001148.4), and full gene synthesis were conducted after codon optimization, and the nucleotide sequences are shown in SEQ ID NO.1~NO. 5, respectively.

MjNadK, EcNadK, CgNadK, EhNadK, ScNadK were cloned into the first polyclonal site of plasmid pCDFDuet-1 using a one-step cloning method.

Vector linearization primer 1 and primer 2 were designed, using 10~15 bp each of the beginning and end of the linearization vector as homologous sequences, primers 3~primer 12 with homologous sequences were designed according to SEQ ID NO.1~NO. 5; using synthetic MjNadK, EcNadK, CgNadK, EhNadK, ScNadK as templates, the homologous arms were added to the 5'end of the gene-specific forward/reverse amplification primer, then the MjNadK, EcNadK, CgNadK, EhNadK, and ScNadK genes with homologous arms were amplified using high-fidelity PfuDNA polymerase, and the PCR products after digestion of the templates were purified and recovered using DNA recovery and purification kits, and the nucleic acid concentrations were measured separately to obtain MjNadK, EcNadK, CgNadK, EhNadK and ScNadK gene sequences with homologous sequences.

Primer 1:
5'-GATCCGAATTCGAGCTCGG-3';

Primer 2:
5'-CTGGCTGTGGTGATGATGGTG-3';

Primer 3:
5'-accatcatcaccacagccagATGGTCATCATGGAAGGGTTTAA-3';

Primer 4:
5'-gccgagctcgaattcggatcTTTAATACCAAGACAGCGACTTAACTT-3';

Primer 5:
5'-accatcatcaccacagccagATGAACAACCACTTCAAGTGCATT-3';

Primer 6:
5'-gccgagctcgaattcggatcAAATAATTTTTTGGACCAGCCTAAC-3';

Primer 7:
5'-accatcatcaccacagccagATGACAGCACCTACCAACGCA-3';

Primer 8:
5'-gccgagctcgaattcggatcCCCTGCGCTGCGCGGGTC-3';

Primer 9:
5'-accatcatcaccacagccagATGACCACATTACAGATTGATCATATTC-3';

Primer 10:
5'-gccgagctcgaattcggatcTTCAAAGAAATCCTTTGTGACTTTATTAAT-3';

Primer 11:
5'-accatcatcaccacagccagATGTTCGTCCGTGTAAAACTTAAT-3';

Primer 12:
5'-gccgagctcgaattcggatcATCATTATCGGTTTGACGCTTC-3';

Single fragment homologous recombination reaction:

Optimal cloning vector usage={0.02*number of base pairs of cloning vector}ng(0.03 pmol)

Optimal amount of insert fragment used={0.04*number of base pairs of insert fragment}ng (0.06 μmol)

Reaction system was as follow.

| component | recombination reaction | negative control 1 | negative control 2 | positive control |
|---|---|---|---|---|
| linearization vector | X μL | X μL | 0 μL | 1 μL |
| Inserted fragment | Y μL | 0 μL | Y μL | 1 μL |
| 2*CLonExpress MIX | 5 μL | 0 μL | 0 μL | 5 μL |
| ddH2O | to 10 μL | to 10 μL | to 10 μL | to 10 μL |

Note:
X indicates the amount of linearized vector added, and Y indicates the amount of inserted fragment.

The configured reaction system was mixed by gently pipetting, and the reaction solution was collected into the bottom of the tube after a short centrifugation. The reaction system was placed in a water bath at 37° C. and left for 30 min, and then immediately cooled on ice. The five different systems were transformed into E. coli BL21 (DE3) MNMN (42° C., 90 s), coated on LB plates containing 50 μg/mL streptomycin resistance and incubated at 37° C. for 12-16 h. The monoclonal extraction plasmids were randomly picked for sequencing and identification, and recombinant strains E. coli BL21(DE3)MN/pCDFDuet-1-MjNadK E. coli BL21(DE3)MN/pCDFDuet-1-EcNadK, E. coli BL21(DE3)MN/pCDFDuet-1-CgNadK, E. coli BL21(DE3)MN/pCDFDuet-1-EhNadK, E. coli BL21(DE3)MN/pCDFDuet-1-ScNadK containing MjNadK, EcNadK, CgNadK, EhNadK, ScNadK genes respectively were separately screened and obtained.

Embodiment 3: Transformation of Cofactor Synthesis Pathway Genes

In this embodiment, the cofactor synthesis metabolic pathway of *E. coli* BL21 (DE3) was searched in the KEGG database, and nadE (NAD synthase gene), nadD (nicotinic acid adenyltransferase gene), and pncB (nicotinic acid phosphoribosyltransferase gene) were obtained with the nucleotide sequences shown in SEQ ID NO.8-NO. 10, respectively.

The nadE, nadD and pncB were cloned into the second polyclonal site of plasmid pCDFDuet-1 using a one-step cloning method.

Primer 13 and primer 14 of vector linearization were designed, and the homologous sequences of 10~15 bp each at the beginning and end of the linearized vector were used to design primers 15~primer 20 with homologous sequences according to SEQ ID NO.8~NO. 10, and the homologous arm was added to the 5' end of the gene~specific forward/reverse amplification primer using the *E. coli* BL21 (DE3) MN genome as the template. The nadE, nadD and pncB genes with homologous arms were amplified by using high fidelity PfuDNA polymerase, and the PCR products after digestion of the template were purified and recovered by DNA recovery and purification kit, and the nucleic acid concentrations were measured separately to obtain the nadE, nadD and pncB gene sequences with homologous sequences and the amplified linearization vector pCDFDuet-1.

```
Primer13:
5'-gcagatctcaattggatatcggc-3';

Primer14:
5'-catatgtatatctccttcttatacttaac-3';

Primer15:
5'-gaaggagatatacatatgATGACATTGCAACAACAA-3';

Primer16:
5'-tccaattgagatctgcTTACTTTTTCCAGA-3';

Primer17:
5'-gaaggagatatacatatgATGAAATCTTTACAGGC-3';

Primer18:
5'-tccaattgagatctgcTCAGCGATACAAG-3';

Primer19:
5'-gaaggagatatacatatgATGACACAATTCGCTTCT-3';

Primer20:
5'-tccaattgagatctgcTTAACTGGCTTTTTTAATATGCG-3';
```

The nadE, nadD, and pncB genes were ligated into pCDFDuet-1 as described in Embodiment 1, and the three different systems were transformed into *E. coli* BL21(DE3) MN (42° C., 90 s), coated on LB plates containing 50 μg/mL streptomycin resistance, and incubated at 37° C. for 12-16 h. The monoclonal extract plasmids were randomly picked for sequencing and identification to separately screen and obtain the recombinant strains *E. coli* BL21(DE3)MN/pCDFDuet-1-nadE, *E. coli* BL21(DE3)MN/pCDFDuet-1-nadD, and *E. coli* BL21(DE3)MN/pCDFDuet-1-pncB containing nadE, nadD, and pncB respectively.

Embodiment 4: Construction of Co-Expressing *Escherichia coli*

Recombinant *E. coli* BL21 (DE3)/pETDuet-1-PPTGDHE3-GDH containing glufosinate dehydrogenase and glucose dehydrogenase has been constructed in the previous work in our laboratory (Patent Publication No. CN109609475A). The *E. coli* BL21(DE3)/pETDuet-1-PPTGDHE3-GDH, *E. coli* BL21(DE3)MN/pCDFDuet-1-MjNadK, *E. coli* BL21(DE3)MN/pCDFDuet-1-EcNadK, *E. coli* BL21(DE3)MN/pCDFDuet-1-CgNadK, *E. coli* BL21 (DE3)MN/pCDFDuet-1-EhNadK, *E. coli* BL21(DE3)MN/pCDFDuet-1-ScNadK, *E. coli* BL21(DE3)MN/pCDFDuet-1-nadE, *E. coli* BL21(DE3)MN/pCDFDuet-1-nadD, *E. coli* BL21(DE3)MN/pCDFDuet-1-pncB were inoculated into LB liquid medium and the plasmids were extracted after 12 h of incubation to obtain plasmids pETDuet-1-PPTGDHE3-GDH, pCDFDuet-1-MjNadK, pCDFDuet-1-EcNadK, pCDFDuet-1-CgNadK, pCDFDuet-1-EhNadK, pCDFDuet-1-ScNadK, pCDFDuet-1-nadE pCDFDuet-1-nadD, pCDFDuet-1-pncB, respectively, and the nucleic acid concentration were measured; 200 ng of pETDuet-1-PPTGDHE3-GDH was taken to mix well separately with 200 ng of pCDFDuet-1-MjNadK, pCDFDuet-1-EcNadK, pCDFDuet-1-CgNadK, pCDFDuet-1-EhNadK, pCDFDuet-1-ScNadK, pCDFDuet-1-nadE pCDFDuet-1-nadD, pCDFDuet-1-pncB respectively, and the eight mixed plasmids were transformed into *E. coli* BL21 (DE3) MN (42° C., 90 s), coated on LB plates containing 50 μg/mL streptomycin and 50 μg/mL ampicillin and incubated at 37° C. for 12 to 16 hours. The monoclonal extract plasmids were randomly selected for sequencing and identification, and recombinant *E. coli* strains *E. coli* BL21(DE3)MN/pETDuet-1-PPTGDHE3-GDH/pCDFDuet-1-MjNadK *E. coli* BL21(DE3)MN/pETDuet-1-PPTGDHE3-GDH/pCDFDuet-1-EcNadK *E. coli* BL21(DE3)MN/pETDuet-1-PPTGDHE3-GDH/pCDFDuet-1-CgNadK *E. coli* BL21(DE3)MN/pETDuet-1-PPTGDHE3-GDH/pCDFDuet-1-EhNadK *E. coli* BL21 (DE3)MN/pETDuet-1-PPTGDHE3-GDH/pCDFDuet-1-ScNadK *E. coli* BL21(DE3)MN/pETDuet-1-PPTGDHE3-GDH/pCDFDuet-1-nadE *E. coli* BL21(DE3)MN/pETDuet-1-PPTGDHE3-GDH/pCDFDuet-1-nadD *E. coli* BL21 (DE3)MN/pETDuet-1-PPTGDHE3-GDH/pCDFDuet-1-pncB which respectively containing PPTGDHE3/GDH/MjNadK PPTGDHE3/GDH/EcNadK PPTGDHE3/GDH/CgNadK, PPTGDHE3/GDH/EhNadK, PPTGDHE3/GDH/ScNadK PPTGDHE3/GDH/nadE, PPTGDHE3/GDH/nadD, PPTGDHE3/GDH/pncB were screened and obtained separately.

Embodiment 5: Induced Expression of Recombinant *Escherichia coli*

(1) Obtaining wet cells of NADH kinase-containing *E. coli*: The five recombinant *E. coli* obtained in Embodiment 1 were inoculated into LB liquid medium containing 50 μg/mL streptomycin resistance, respectively, and incubated at 37° C., 200 rpm for 12 h. Then, they were inoculated into fresh LB liquid medium containing 50 μg/mL streptomycin resistance at a 1% (v/v) inoculum, and incubated at 37° C. After incubation for 16 h at 24° C., the culture was induced by centrifugation at 4° C. and 8000 rpm for 10 min, and the supernatant was discarded and the precipitate was collected and washed twice with 20 mM phosphate buffer (PBS) at pH 7.5 to obtain wet cells of recombinant *E. coli* BL21(DE3)MN/pCDFDuet-1-MjNadK, *E. coli* BL21(DE3)MN/pCDFDuet-1-EcNadK, *E. coli* BL21(DE3)MN/pCDFDuet-1-CgNadK, *E. coli* BL21 (DE3)MN/pCDFDuet-1-EhNadK, *E. coli* BL21(DE3) MN/pCDFDuet-1-ScNadK containing MjNadK, EcNadK, CgNadK and EhNadK. CgNadK, EhNadK, ScNadK.

Figure 2:
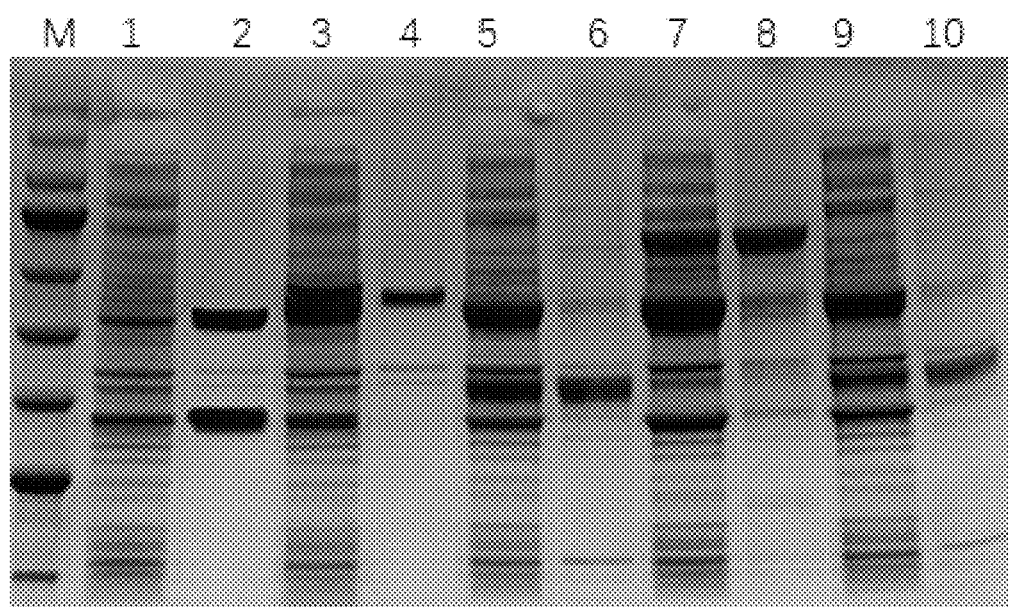
FIG. 2 shows the SDS-PAGE protein electrophoresis of crude enzyme solution of co-expressing strains co-expressing each of five kinds of NAD(H) kinase, glufosinate dehydrogenase and glucose dehydrogenase. M: standard protein molecular weight; lane 1: supernatant of E. coli BL21(DE3)MN/pETDuet-1-PPTGDHE3-GDH/pCDFDuet-1-EhNadK crude enzyme solution; lane 2: E. coli BL21(DE3)MN/pETDuet-1-PPTGDHE3-GDH/pCDFDuet-1-EhNadK crude enzyme solution precipitate; lane 3: E. coli BL21(DE3)MN/pETDuet-1-PPTGDHE3-GDH/pCDFDuet-1-ScNadK Crude enzyme solution supernatant; lane 4: E. coli BL21(DE3)MN/pETDuet-1-PPTGDHE3-GDH/pCDFDuet-1-ScNadK crude enzyme solution precipitate; lane 5: E. coli BL21(DE3)MN/pETDuet-1-PPTGDHE3-GDH/pCDFDuet-1-ScNadK crude enzyme solution supernatant; lane 6: E. coli BL21(DE3)MN/pETDuet-1-PPTGDHE3-GDH/pCDFDuet-1 EcNadK crude enzyme solution supernatant; lane 6: E. coli BL21(DE3)MN/pETDuet-1-PPTGDHE3-GDH/pCDFDuet-1-EcNadK crude enzyme solution precipitate; lane 7: E. coli BL21(DE3)MN/pETDuet-1-PPTGDHE3-GDH/pCDFDuet-1-MjNadK crude enzyme solution supernatant; lane 8: E. coli BL21(DE3)MN/pETDuet-1-PPTGDHE3-GDH/pCDFDuet-1-MjNadK crude enzyme solution precipitate; lane 9: E. coli BL21(DE3)MN/pETDuet-1-PPTGDHE3-GDH/pCDFDuet-1-CgNadK crude enzyme solution supernatant; lane 10: E. coli BL21(DE3)MN/pETDuet-1-PPTGDHE3-GDH/pCDFDuet-1-CgNadK crude enzyme solution precipitate.
Figure 3:
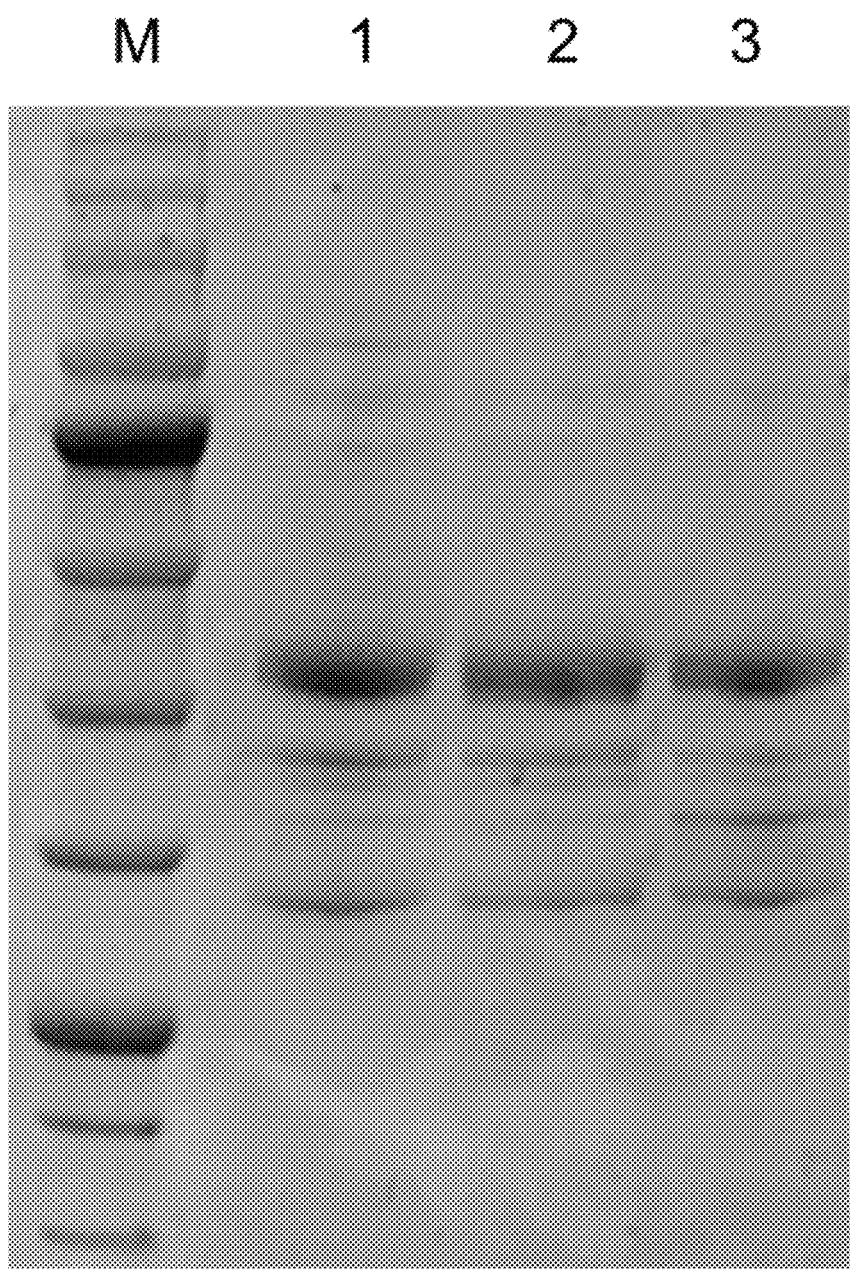
FIG. 3 shows the SDS-PAGE protein electrophoresis of crude enzyme solution of three co-expressing strains that co-expressing glufosinate dehydrogenase, glucose dehydrogenase and each of nadD, nadE, pncB. M: standard protein molecular weight; lane 1: E. coli BL21(DE3)MN/pETDuet-1-PPTGDHE3-GDH/pCDFDuet-1-nadD crude enzyme solution; lane 2: E. coli BL21(DE3)MN/pETDuet-1-PPTGDHE3-GDH/pCDFDuet-1-nadE crude enzyme solution; lane 3: E. coli BL21(DE3)MN/pETDuet-1-PPTGDHE3-GDH/pCDFDuet-1-pncB crude enzyme solution.

(2) Acquisition of wet cells of *E. coli* containing cofactor synthesis pathway enzymes: The three recombinant *E. coli* obtained in Embodiment 3 were inoculated into LB liquid medium containing 50 μg/mL streptomycin resistance, respectively, and incubated at 37° C., 200 rpm for 12 h. Then, 1% (v/v) inoculum of them were inoculated into fresh LB liquid medium containing 50 μg/mL streptomycin resistance, and incubated at 37° C., 150 rpm until cell OD600 reached 0.6~ 0.8. IPTG with a final concentration of 0.1 mmM was added, after incubation for 16 h at 24° C. and induction at 8,000 rpm for 10 min, the supernatant was discarded and the precipitate was collected and washed twice with 20 mM phosphate buffer (PBS) at pH 7.5, then wet bacteria of *E. coli* BL21(DE3)MN/pCDFDuet-1-nadD, *E. coli* BL21(DE3)MN/pCDFDuet-1-nadE, *E. coli* BL21 (DE3)MN/pCDFDuet-1-nadE, and *E. coli* BL21(DE3) MN/pCDFDuet-1-pncB with recombinant strains containing NAD synthase, nicotinic acid adenylate transferase and nicotinic acid phosphate ribosyl transferase were obtained. (3) Acquisition of co-expressing *E. coli* wet cells: the five recombinant *E. coli* obtained in Embodiment 4 were inoculated into LB liquid medium containing 50 μg/mL streptomycin and 50 μg/mL ampicillin resistance, respectively, and incubated at 37° C., 200 rpm for 12 h. Then, they were inoculated at 1% (v/v) inoculum into fresh LB liquid medium containing 50 μg/mL streptomycin and 50 μg/mL ampicillin resistance, incubated at 37° C., 150 rpm until the OD600 of the bacterium reached 0.6-0.8, added IPTG at a final concentration of 0.1 mM, induced at 24° C. for 16 h, then centrifuged at 4° C., 8000 rpm for 10 min, discarded the supernatant, collected the precipitate, washed twice with pH 7.5, 20 mM phosphate buffer (PBS), to obtain the wet cells of recombinant strains *E. coli* BL21(DE3)MN/pETDuet-1-PPTGDHE3-GDH/pCDFDuet-1-MjNadK, *E. coli* BL21(DE3)MN/pETDuet-1-PPTGDHE3-GDH/pCDFDuet-1-EcNadK, *E. coli* BL21(DE3)MN/pETDuet-1-PPTGDHE3-GDH/pCDFDuet-1-CgNadK, *E. coli* BL21(DE3)MN/pETDuet-1-PPTGDHE3-GDH/pCDFDuet-1-EhNadK, *E. coli* BL21(DE3)MN/pETDuet-1-PPTGDHE3-GDH/pCDFDuet-1-ScNadK, *E. coli* BL21(DE3)MN/pETDuet-1-PPTGDHE3-GDH/pCDFDuet-1-nadE, *E. coli* BL21(DE3)MN/pETDuet-1-PPTGDHE3-GDH/pCDFDuet-1-nadD, *E. coli* BL21 (DE3)MN/pETDuet-1-PPTGDHE3-GDH/pCDFDuet-1-pncB; the protein expressions are shown in FIG. 2 and FIG. 3.

Embodiment 6: Determination of Intracellular Cofactor NADP(H) Concentration

Cofactors were determined using EnzyChrom™ NADP/NADPH Assay Kit. The fermentation broth was diluted to an OD600 of about 0.5, 1 mL of the diluted fermentation broth was taken, centrifuged at 12000 rpm for 1 min, the supernatant was discarded and washed with PBS buffer and the supernatant was discarded by centrifugation again, 100 μL of NADP extract (NADPH extract) was added and held at 60° C. for 5 min for the extraction of NADP (NADPH), followed by 20 μL of Assay Buffer and 100 μL of the opposite extraction solution for neutralization, centrifuged at 14000 rpm for 5 min, the supernatant was used for the determination; 40 μL of sample and 80 μL of reaction solution were added to the 96-well enzyme standard plate, OD565 was measured immediately, and OD565 was measured again after holding at 28° C. for 30 min, and the cofactor concentration was calculated using the difference between before and after OD565 and the corresponding standard curve. The cofactor concentration was calculated by using the difference between the OD565 and the corresponding standard curve.

The reaction solution formulation was 60 μL of Assay Buffer, 1 μL of Enzyme Mix, 10 μL of Glucose, 14 μL of MTT.

Figure 4:
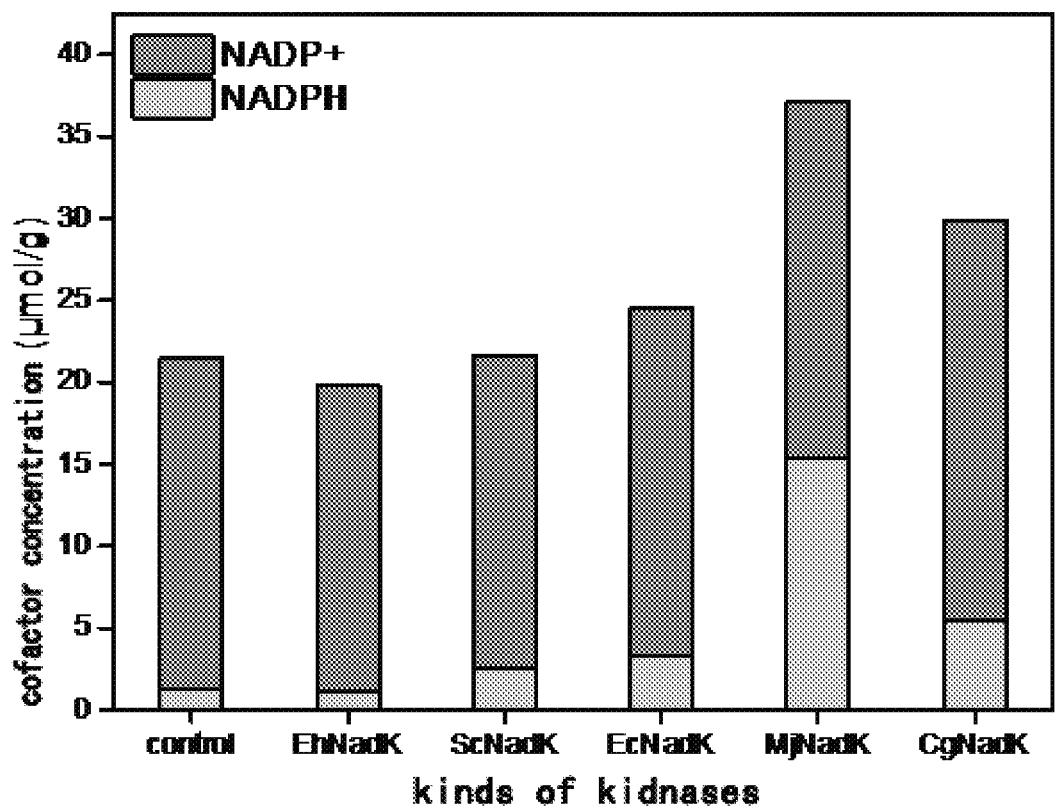
FIG. 4 shows the changes of cofactor NADP (H) after expression of EhNadK, ScNadK, MjNadK, EcNadK, CgNadK by E. coli BL21 (DE3).

The concentration of NADP(H) in recombinant *E. coli* BL21(DE3)MN/pCDFDuet-1-MjNadK, *E. coli* BL21(DE3) MN/pCDFDuet-1-EcNadK, *E. coli* BL21(DE3)MN/pCDFDuet-1-CgNadK, *E. coli* BL21(DE3)MN/pCDFDuet-1-EhNadK and *E. coli* BL21(DE3)MN/pCDFDuet-1-ScNadK containing different NADH kinases are shown in FIG. 4. From FIG. 4, it can be seen that the intracellular NADP(H) in cells expressing MjNadK, EcNadK, and CgNadK was increased by 14.2%~71.4%, while NADP(H) was not increased in cells expressing EhNadK and ScNadK, so the preferred NAD kinase was MjNadK.

Figure 5:
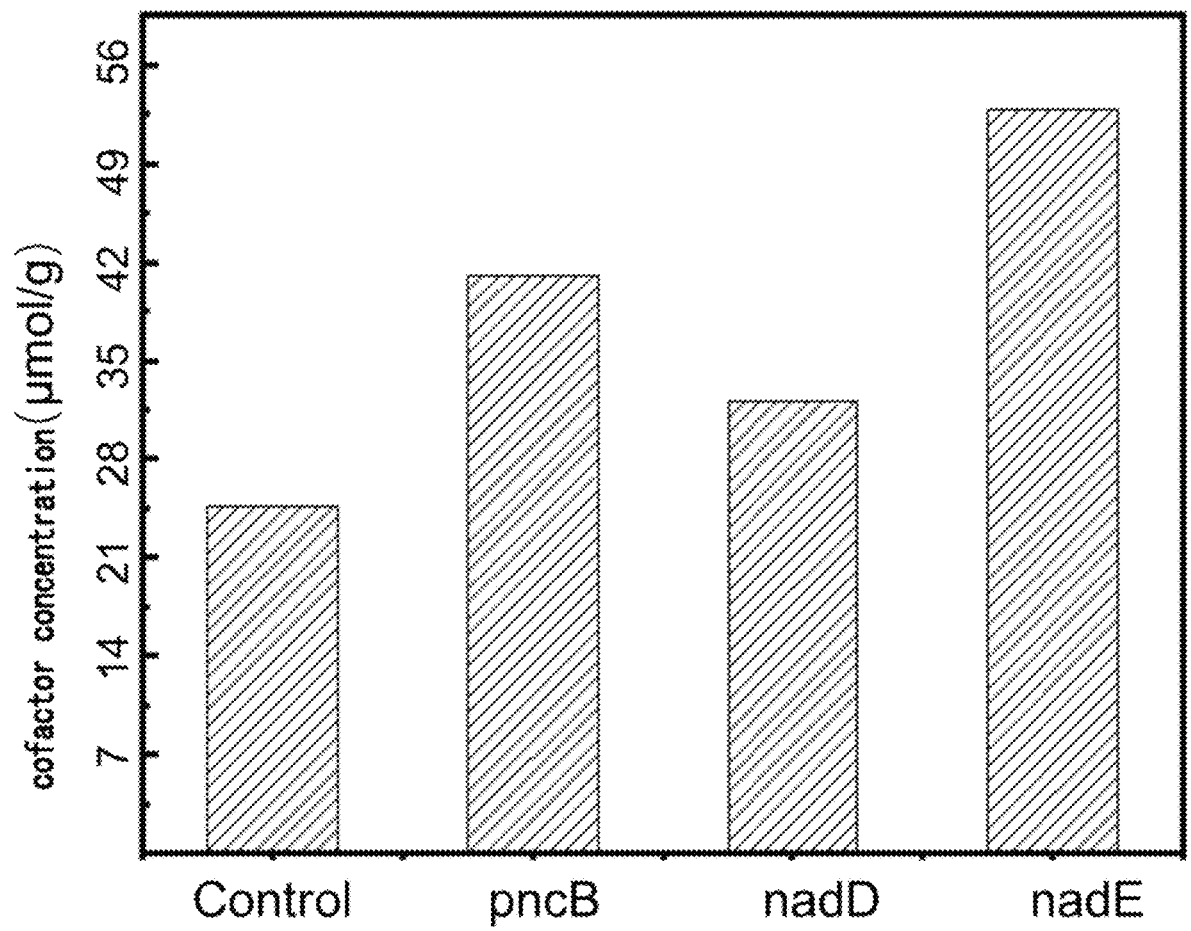
FIG. 5 shows the changes of cofactor NADP (H) after expression of nadD, nadE, pncB in E. coli BL21 (DE3).

The concentrations of NADP(H) in recombinant *E. coli* BL21(DE3)MN/pCDFDuet-1-nadD, *E. coli* BL21(DE3) MN/pCDFDuet-1-nadE, *E. coli* BL21(DE3)MN/pCDFDuet-1-pncB containing different cofactor synthesis pathway enzymes are shown in FIG. 5. From FIG. 5, it can be seen that intracellular NADP(H) was increased by 114.5% and 70.3% after expression of nadE and pncB, respectively, while NADP(H) was not increased after expression of nadD. So the preferred cofactor synthesis pathway enzyme was nadE.

Figure 6:
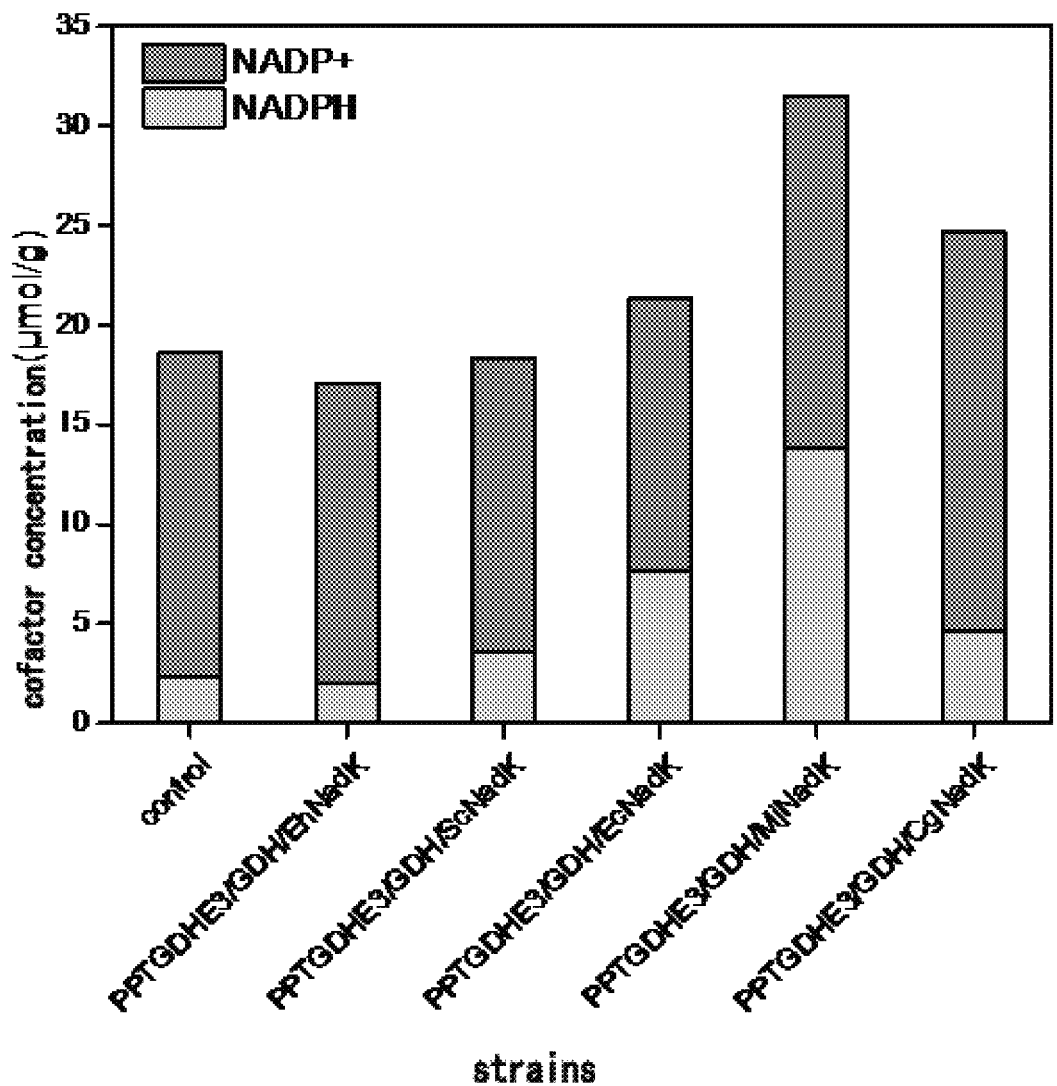
FIG. 6 shows the intracellular cofactor NADP (H) changes after expression of nadD, nadE, and pncB in strains E. coli BL21(DE3)MN/pETDuet-1-PPTGDHE3-GDH/pCDFDuet-1-EhNadK, E. coli BL21(DE3)MN/pETDuet-1-PPTGDHE3-GDH/pCDFDuet-1-ScNadK, E. coli BL21(DE3)MN/pETDuet-1-PPTGDHE3-GDH/pCDFDuet-1-EcNadK, E. coli BL21(DE3)MN/pETDuet-1-PPTGDHE3-GDH/pCDFDuet-1-MjNadK, E. coli BL21(DE3)MN/pETDuet-1-PPTGDHE3-GDH/pCDFDuet-1-MjNadK, E. coli BL21(DE3)MN/pETDuet-1-PPTGDHE3-GDH/pCDFDuet-1-EcNadK, E. coli pETDuet-1-PPTGDHE3-GDH/pCDFDuet-1-CgNadK.

The results of NADP (H) concentration measurements in *E. coli* containing different NADH kinases co-expressed with glufosinate dehydrogenase and glucose dehydrogenase are shown in FIG. 6. From FIG. 6, it can be seen that NADP (H) was increased by 16.7%~77.2% in MjNadK, EcNadK, and CgNadK co-expressing strains, and NADP (H) was not improved.

Figure 7:
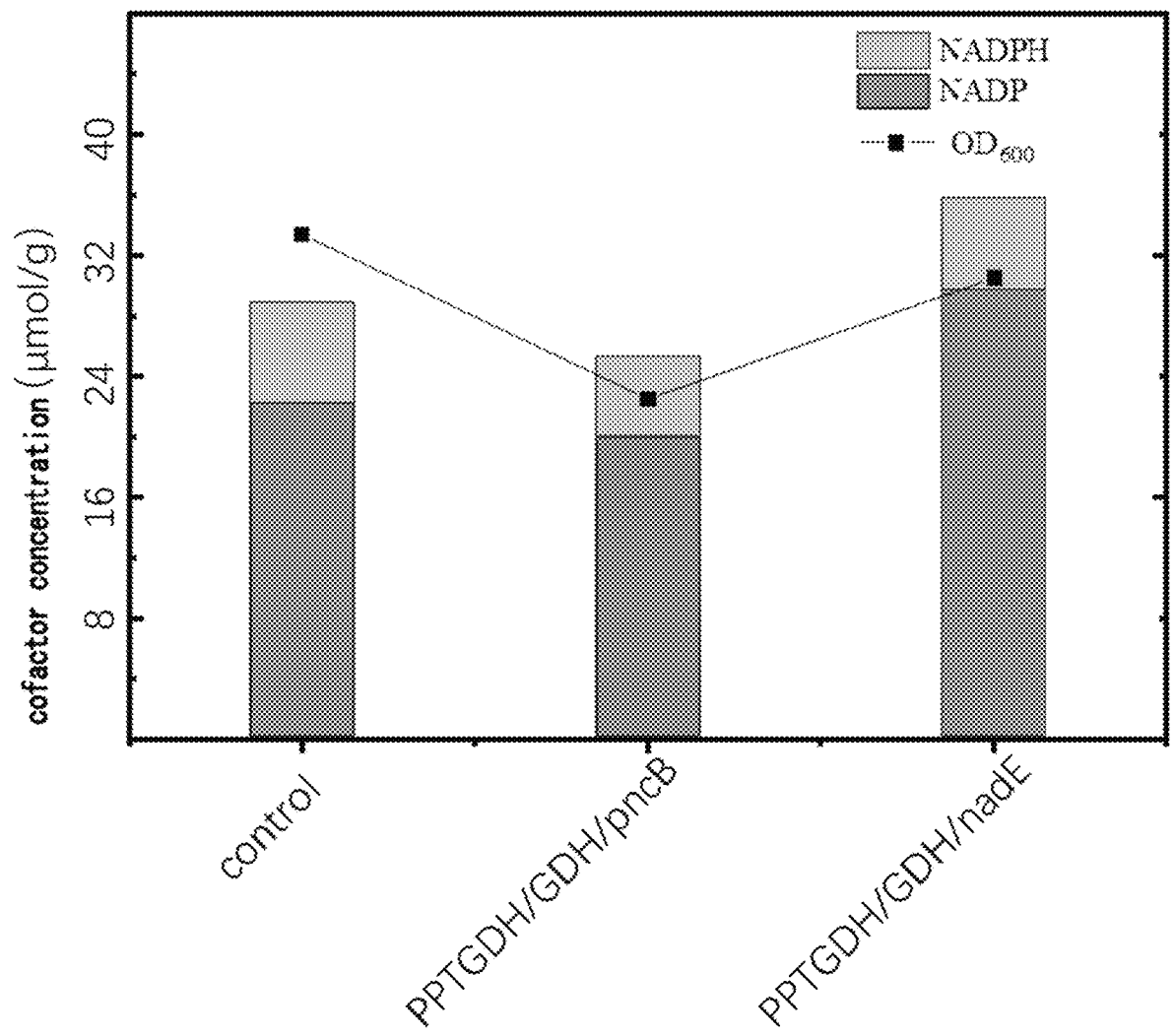
FIG. 7 shows the intracellular cofactor NADP (H) changes of strains E. coli BL21(DE3)MN/pETDuet-1-PPTGDHE3-GDH/pCDFDuet-1-pncB, E. coli BL21(DE3)MN/pETDuet-1-PPTGDHE3-GDH/pCDFDuet-1-nadE.

The results of NADP (H) concentration measurements in *E. coli* containing different cofactor synthesis pathway enzymes co-expressed with glufosinate dehydrogenase and glucose dehydrogenase are shown in FIG. 7. From FIG. 7, it can be seen that co-expression of the nadE gene increased the cofactor content by 41% compared to the control.

Embodiment 7: Construction of MjNadK/nadE/PPTGDH/GDH Co-Expressing Strain

Using pCDFDuet-1-MjNadK as a vector, linearized using primers 13 and 14, and taking the *E. coli* BL21 (DE3) genome as a template, amplified using primers 15 and 16, and the recombinant vector pCDFDuet-1-MjNadK-nadE was constructed according to the recombinant vector construction method described in Embodiment 2.

Co-transform pETDuet-1-PPTGDH3-GDH and pCDFDuet-1-MjNadK-nadE into *E. coli* BL21(DE3) MN by the method described in Embodiment 4, and screen positive clones to obtain MjNadK/nadE/PPTGDH/GDH co-expressing strain.

MjNadK/nadE/PPTGDH3/GDH co-expressing *E. coli* wet cells were obtained by the method described in Embodiment 5.

The concentrations of NADP$^+$ and NADPH cofactor in MjNadK/nadE/PPTGDH3/GDH co-expressing *E. coli* were assayed according to the method described in Embodiment 6, and the results are shown in the following table.

| strain | Concentration of NADP⁺(μmol/g) | Concentration of NADPH(μmol/g) | Concentration of total cofactors(μmol/g) |
| --- | --- | --- | --- |
| Control | 2.8 | 17.3 | 20.1 |
| MjNadK/nadE/PPTGDH/GDH co-expressing *E. coli* | 30.1 | 6.7 | 36.8 |

Embodiment 8: Recombinant *E. coli* Activity Assay

The wet cells obtained in Embodiment 4 and Embodiment 7 were taken and resuspended with 100 mM potassium phosphate buffer (pH 7.5) into 100 g/L bacterial suspension; 400 mM of 2-carbonyl-4-(hydroxymethylphosphinyl)-butyric acid, 500 mM of glucose, and 600 mM of ammonium sulfate were configured respectively. The reaction system was:

250 μL of 2-carbonyl-4-(hydroxymethylphosphinyl)-butyric acid;
250 μL of glucose;
250 μL of ammonium sulfate;
100 μL of bacterial suspension;
Potassium phosphate buffer (pH 7.5) 150 μL.

The reaction was carried out at 35° C. and 600 rpm for 10 min, 100 μL of sample was taken, and the reaction was terminated with 5 μL of 6M HCl, diluted 100 times and then the amount of 2-carbonyl-4-(hydroxymethylphosphinyl)-butyric acid reduced and the amount of L-glufosinate produced were detected by high performance liquid chromatography.

The method of detecting 2-carbonyl-4-(hydroxymethylphosphinyl)-butyric acid is as follow.

Chromatographic column type: QS-C18, 5 μm, 4.6×250 mm; mobile phase: 5.75 g of dihydrogen phosphate was dissolved in 800 mL of ultrapure water, 1 g of tetrabutylammonium hydroxide was added and diluted with water and fixed to 1000 mL, the pH was adjusted to 3.8 with phosphoric acid, and mixed with acetonitrile at a volume ratio of 88:12. The detection wavelength was 232 nm; flow rate: 1.0 mL/min; column temperature: 40° C.; the peak time of 2-carbonyl-4-(hydroxymethylphosphinyl)-butyric acid was: 9.7 min.

The detection of glufosinate was performed by high performance liquid chromatography with pre-column derivatization as follows.

Chromatographic conditions: column type: QS-C18, 5 μm, 4.6×250 mm; mobile phase: 50 mM ammonium acetate solution: methanol=10:1; fluorescence detection wavelength: λ ex=340 nm, λ em=455 nm; flow rate: 1 mL/min; column temperature: 30° C.; peak time of L-glufosinate was 8.5 min, peak time of D-glufosinate was 10.2 min.

Derivatization reagent: 0.1 g of o-phthalaldehyde and 0.12 g of N-acetyl-L-cysteine were weighed and dissolved with 10 mL of ethanol, then 40 mL of 0.1 moL/L borate buffer (pH9.8) was added and shaken to dissolve fully, and stored in the refrigerator at 4° C.

Derivatization reaction and determination: 200 μL of sample was added into 400 μL of derivatization reagent, shaken at 500 rpm for 5 min at 30° C. on an oscillator, then 400 μL of ultrapure water was added and mixed, and 10 μL of sample was injected for HPLC analysis.

The concentration-peak area standard curve was plotted using 2-carbonyl-4-(hydroxymethylphosphinyl)-butyric acid and glufosinate standards, and the sample concentration was calculated using the standard curve, and the cell activity was calculated based on the product generation. Wherein activity unit was defined as: the amount of wet cells required to catalyze the generation of 1 μmol L-glufosinate in 1 min was defined as 1 U. Specific activity was defined as: the number of activity units per gram of wet cells.

Figure 8:
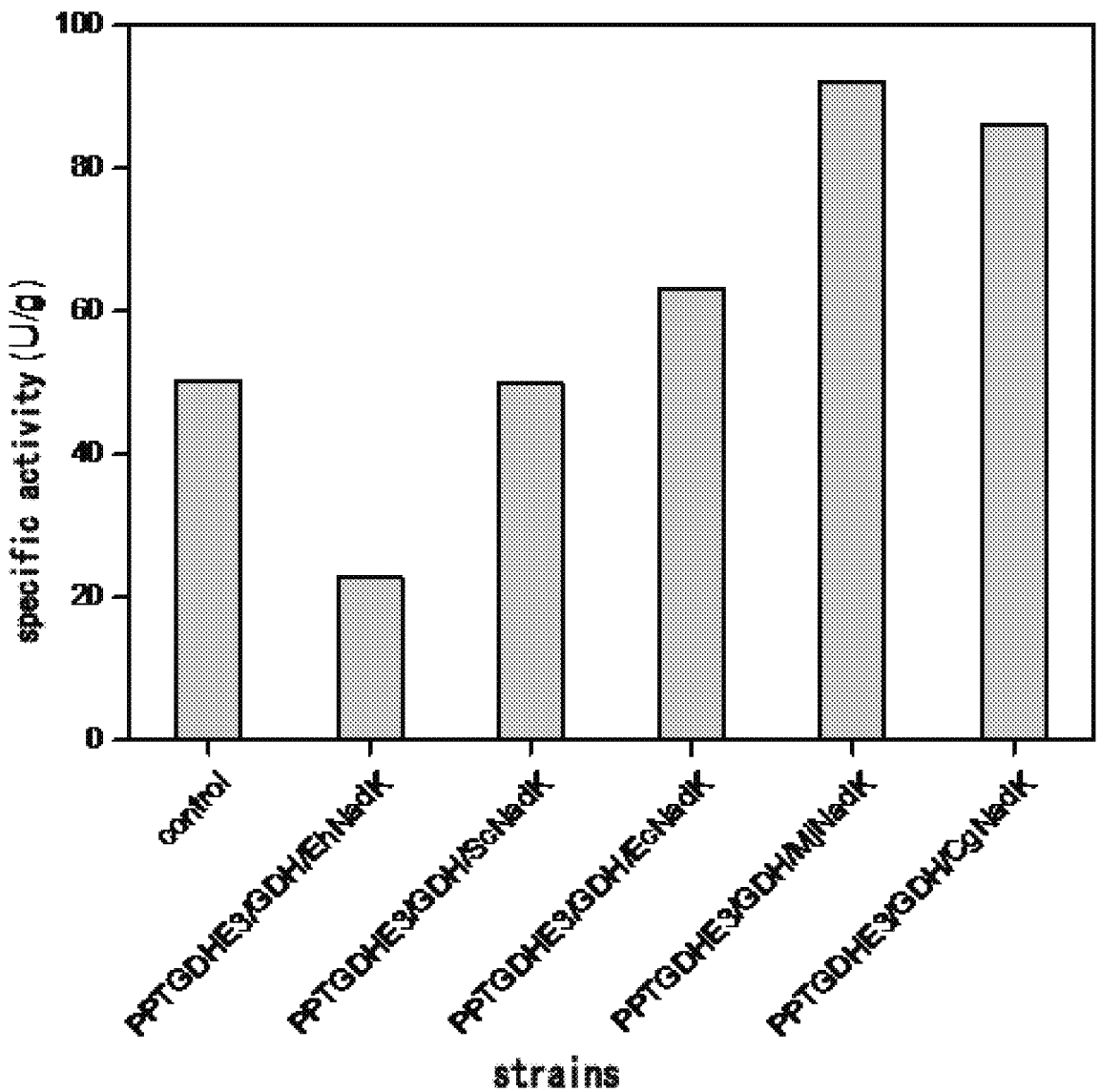
FIG. 8 shows the whole cell specific activity results in strains E. coli BL21(DE3)MN/pETDuet-1-PPTGDHE3-GDH/pCDFDuet-1-EhNadK, E. coli BL21(DE3)MN/pETDuet-1-PPTGDHE3-GDH/pCDFDuet-1-ScNadK, E. coli BL21(DE3)MN/pETDuet-1-PPTGDHE3-GDH/pCDFDuet-1-EcNadK, E. coli BL21(DE3)MN/pETDuet-1-PPTGDHE3-GDH/pCDFDuet-1-MjNadK, E. coli BL21(DE3)MN/pETDuet-1-PPTGDHE3-GDH/pCDFDuet-1-MjNadK, E. coli BL21(DE3)MN/pETDuet-1-PPTGDHE3-GDH/pCDFDuet-1-EcNadK, E. coli pETDuet-1-PPTGDHE3-GDH/pCDFDuet-1-CgNadK.

The specific activity of NADH kinase, glufosinate dehydrogenase, and glucose dehydrogenase co-expressed in *E. coli* obtained in Embodiment 4 is shown in FIG. 8. As shown in FIG. 8, the introduction of different NADH kinases increased the specific activity of cells by 25.6% to 83.1%.

Figure 9:
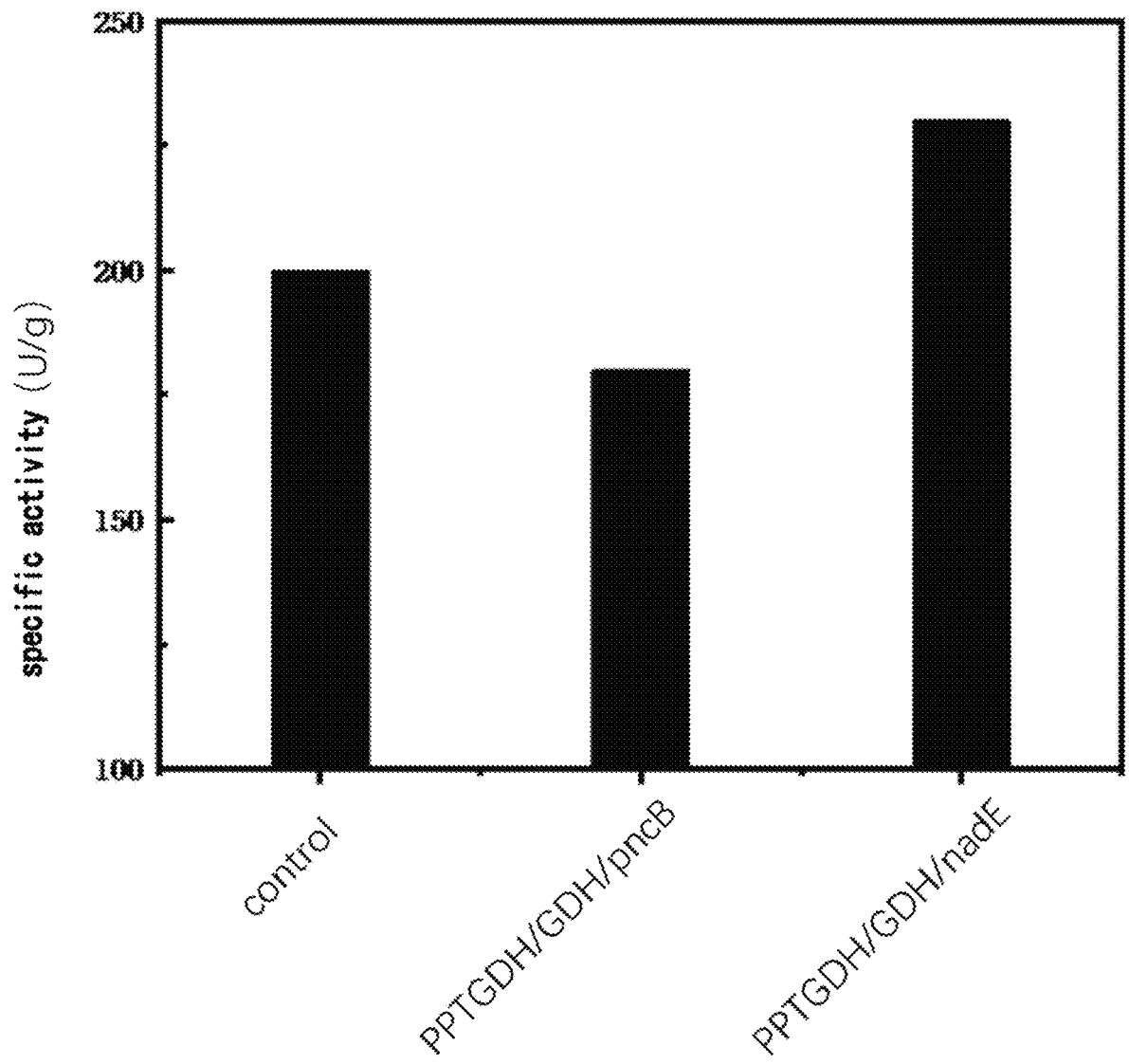
FIG. 9 shows the results of whole cell specific activity of strains E. coli BL21(DE3)MN/pETDuet-1-PPTGDHE3-GDH/pCDFDuet-1-pncB, E. coli BL21(DE3)MN/pETDuet-1-PPTGDHE3-GDH/pCDFDuet-1-nadEqu.

The specific activity of co-expressing *E. coli* obtained in Embodiment 4 that co-expressed cofactor synthesis pathway enzymes, glufosinate dehydrogenase and glucose dehydrogenase is shown in FIG. 9. As shown in FIG. 9, the specific activity was increased by 12.5% after the introduction of nadE compared to the control.

The specific activity of MjNadK/nadE/PPTGDH/GDH co-expressing *E. coli* obtained in Embodiment 7 is as shown in the table below.

| strain | specific activity(U/g) | relative activity(%) |
| --- | --- | --- |
| Control | 54.2 | 100 |
| MjNadK/nadE/PPTGDH/GDH co-expressing *E. coli* | 132.7 | 244.8 |

Embodiment 9: Preparation of Cofactor Self-Sufficient Recombinant *E. coli* Wet Cells Single colonies of recombinant *E. coli* obtained in Embodiment 7 were inoculated into LB liquid medium containing 50 μg/mL ampicillin and streptomycin resistance, incubated at 37° C. for 12 h at 200 rpm, and then inoculated into fresh fermentation medium containing 50 μg/mL ampicillin and streptomycin resistance at 1% (v/v) inoculum, wherein the fermentation medium contained 0~40 mg/L of L-aspartic acid, quinolinic acid, nicotinic acid, nicotinamide, adenine and ATP, incubated at 37° C., 150 rpm until the OD600 of the bacteria reached 0.6-0.8, added IPTG at a final concentration of 0.1 mM, and incubated at 24° C. for 16 h after induction, centrifuged at 4° C., 8000 rpm for 10 min, discarded the supernatant, collected the precipitate, and incubated with pH 7.5, 20 mM phosphate buffer solution (PBS) twice to obtain wet bacteria.

The composition of fermentation medium was as follows: peptone 24 g/L, yeast powder 16 g/L, NaCl 5 g/L, NaSO₄ 2 g/L, (NH₄)₂SO₄ 2.5 g/L, NH₄Cl 0.5 g/L, citric acid monohydrate 1 g/L, K₂HPO₄-3H₂O 19.12 g/L, NaH₂PO₄-2H₂O 3.6 g/L, MgSO₄-7H₂O 2 g/L, amino acid or pyridine compound 20 mg/L, glycerol 8 g/L, trace metal solution 1 mL/L, defoamer 1 mL/L, solvent is water; where the trace metal solution composition is as follows: $FeSO_4\text{-}7H_2O$ 10 g/L, $CaCl_2$) 2 g/L, $ZnSO_4\text{-}7H_2O$ 2.2 g/L, $MnSO_4\text{-}4H_2O$ 0.5 g/L, $CuSO_4\text{-}5H_2O$ 1 g/L, $(NH_4)_6Mo_7O_{24}\text{-}4H_2O$ 0.1 g/L, $NaB_4O_7\text{-}10H_2O$ 0.02 g/L, and the solvent was water.

The intracellular cofactor concentrations of the wet bacterial bodies obtained from the culture were measured by the method described in Embodiment 6, and the cofactor concentrations were increased by the addition of L-aspartic acid, quinolinic acid, nicotinic acid and nicotinamide, wherein the optimum addition of quinolinic acid was 20 mg/L and the cofactor concentration was increased by 23.8%; the optimum addition of L-aspartic acid was 20 mg/L and the cofactor concentration was increased by 52.3%; the optimum addition of niacin was 30 mg/L, which increased the concentration of cofactor by 27.6%; the optimum addition of nicotinamide was 10 mg/L, which increased the concentration of cofactor by 14.3%; while adenine and ATP did not increase the concentration of cofactor at different addition concentrations, both of them led to the decrease of cofactor concentration at high concentration.

Figure 10:
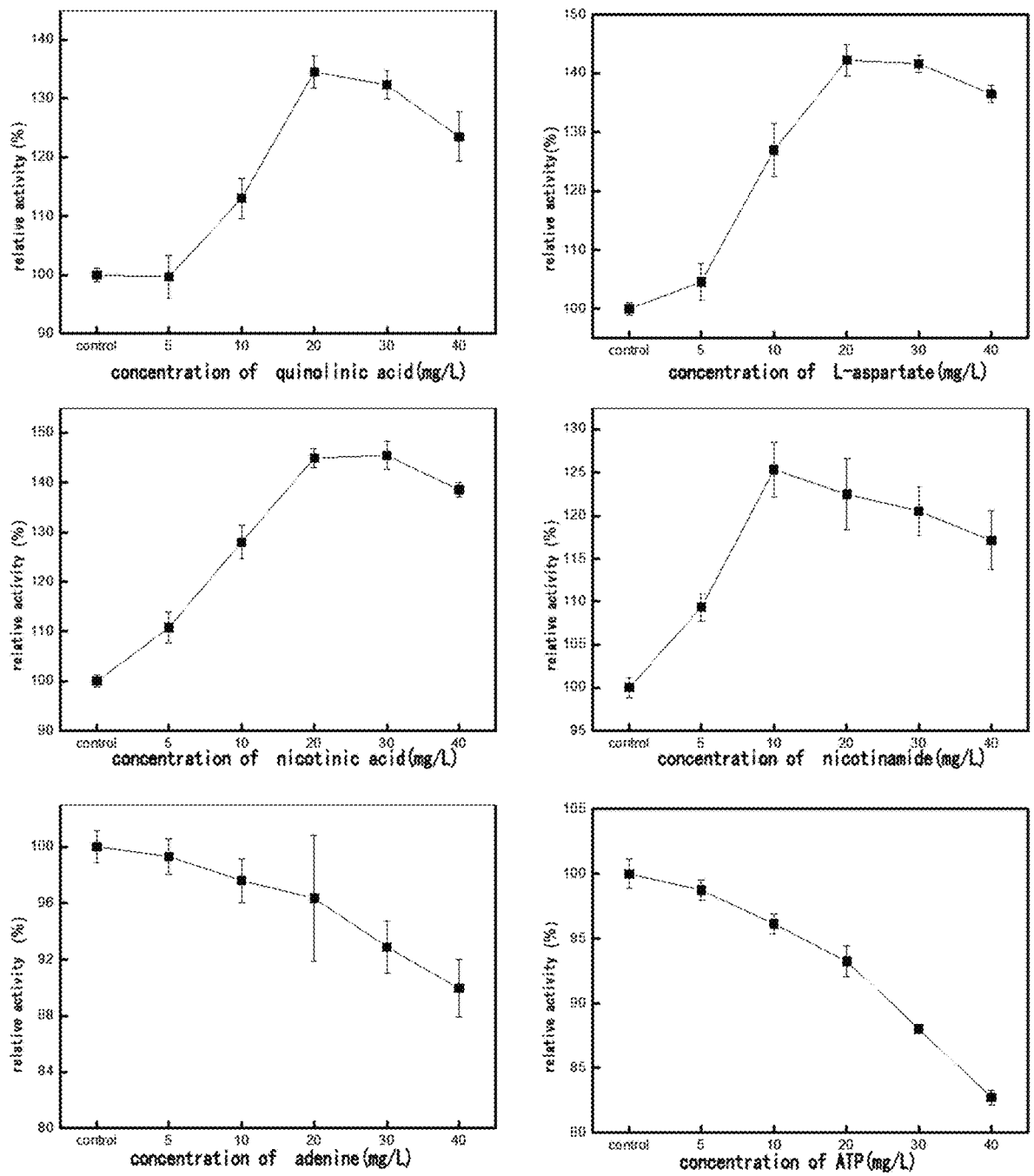
FIG. 10 shows the change in catalytic activity of cells obtained from fermentation after the addition of different concentrations of quinolinic acid, L-aspartic acid, nicotinic acid, nicotinamide, adenine, and ATP to the culture medium.

The specific activity of the wet bacterial cells obtained by the method described in Embodiment 8 was measured, as shown in FIG. 10, the activity was increased by 33.4% with the addition of quinolinic acid at 20 mg/L; 41.7% with the addition of L-aspartic acid at 20 mg/L; 43.9% with the addition of nicotinic acid at 30 mg/L; 26.5% with the addition of nicotinamide at 10 mg/L, while the activity of the addition of adenine and ATP did not result in an increase in activity.

Preferably, the cofactor synthesis precursor addition was L-aspartate 20 mg/L.

Embodiment 10: MjNadK/nadE/PPTGDH/GDH Co-Expressing *E. coli* Catalyzing Synthesis of L-Glufosinate The recombinant *E. coli* wet cell containing MjNadK/nadE/PPTGDH/GDH was obtained by fermentation according to the method described in Embodiment 7, and the catalytic synthesis of L-glufosinate was carried out using a mechanical stirred reactor with a volume of 1 L. The specific reaction system was as follows:
  15 g/L, 20 g/L and 25 g/L for wet cells, respectively;
  2-carbonyl-4-(hydroxymethylphosphinyl)-butyric acid 200 mM;
  250 Mm of glucose;
  300 mM of ammonium sulfate;
  Distilled water fixed to 300 Ml;

The pH was controlled at 7.5 by automatic addition of 15% ammonia, the temperature was controlled at 35° C. by jacket heating and cooling water, and the speed was set at 500 rpm.

Figure 11:
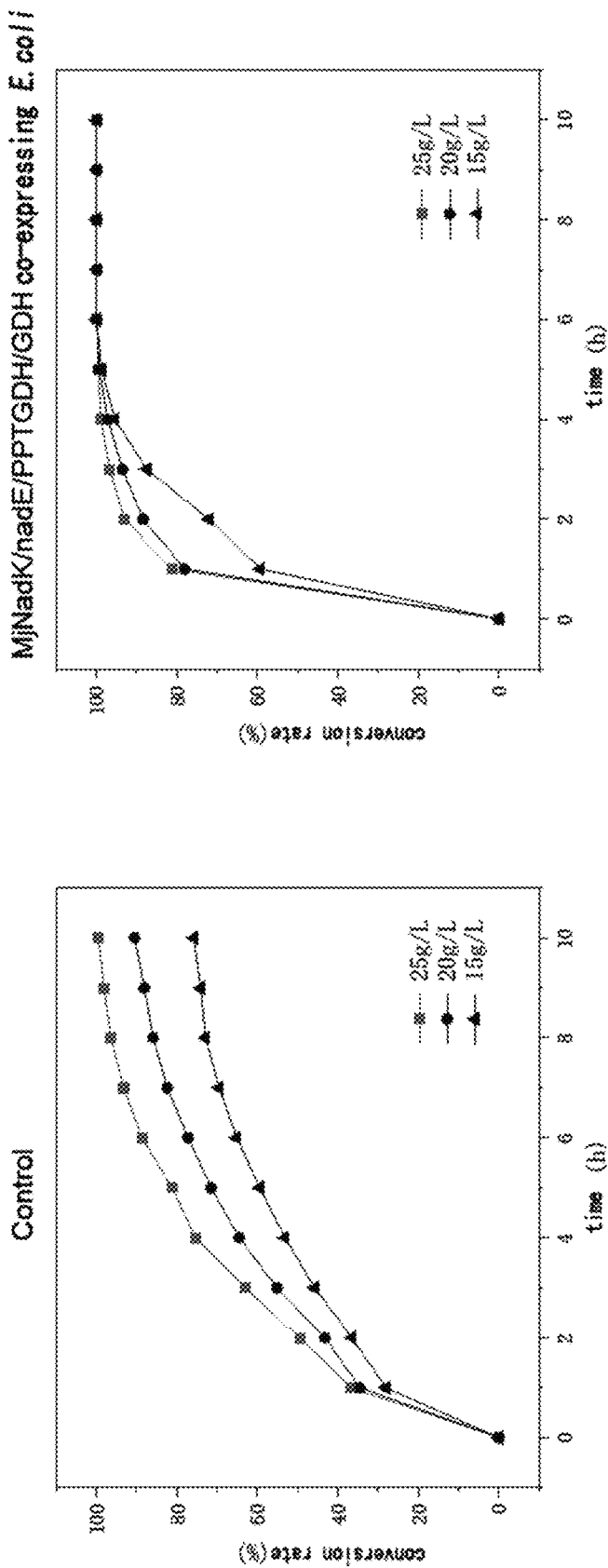
FIG. 11 shows the reaction process of the departure strain and MjNadK/nadE/PPTGDH/GDH co-expressing E. coli catalyzing 2-carbonyl-4-(hydroxymethylphosphinyl)-butyric acid at different bacterial cell concentrations.

The reaction process is shown in FIG. 11. *E. coli* BL21 (DE3)-pETDuet-1-PPTGDH3/GDH, used as a control, required 10 h at 25 g/L to achieve complete transformation of the substrate, while MjNadK/nadE/PPTGDH/GDH co-expressing *E. coli* only required 4 h under the same conditions, and still required only 5 h to achieve the complete reaction when the amount of bacteria cells was reduced to 15 g/L.

What is claimed is:

1. A cofactor self-sufficient *Escherichia coli*, obtained by a constructing methods as follows:
   (1) constructing one or more plasmids or expression vectors capable of intracellular linearization and self-recombination that comprise target genes including a NADH kinase gene, a glucose dehydrogenase gene, a glufosinate dehydrogenase gene and a gene of a NADP cofactor synthesis pathway;
   transforming the one or more plasmids or expression vectors comprising the target genes into an *Escherichia coli* named *E. coli* BL21 (DE3); and
   obtaining a transformed *Escherichia coli* with introduction of the one or more plasmids or expression vectors comprising the target genes that is a glufosinate dehydrogenase-glucose dehydrogenase-NADH kinase co-expressing gene engineering bacterium; wherein said NADH kinase gene sequence is one of SEQ ID NOS: 1 to 3, said glucose dehydrogenase gene sequence is as shown in SEQ ID NO: 6, said glufosinate dehydrogenase gene sequence is as shown in SEQ ID NO: 7, and said NADP cofactor synthesis pathway gene sequence is as shown in one of SEQ ID NOS: 8 and 10; and
   (2) knocking out of any one or a combination of mazG and nadR genes in the genome of the co-expressing gene engineering bacterium to obtain said cofactor self-sufficient *Escherichia coli*.

2. The cofactor self-sufficient *Escherichia coli* of claim 1, wherein the sequence of said NADH kinase gene in step (1) is as shown in SEQ ID NO: 3, and the sequence of said NADP cofactor synthesis pathway gene is as shown in SEQ ID NO: 8.

3. The cofactor self-sufficient *Escherichia coli* of claim 1, wherein the mazG and nadR genes are knocked out in step (2).

4. A method for preparing L-glufosinate, comprising:
   performing a fermentation culture of the cofactor self-sufficient *Escherichia coli* of claim 1, and preparing wet bacterial cells of the cofactor self-sufficient *Escherichia coli* from the fermentation culture;
   preparing a reaction medium containing the wet bacterial cells or an enzyme solution obtained by ultrasonic crushing of the wet bacterial cells as a catalyst, 2-carbonyl-4-(hydroxymethylphosphinyl)-butyric acid as a substrate, ammonium sulfate, and glucose, wherein the reaction medium is buffered at pH 7.5;
   reacting the reaction medium at 35 to 40° C. with shaking at 500 to 600 rpm; and
   purifying L-glufosinate from the reaction medium.

5. The method of claim 4, wherein the reaction medium comprises the wet bacterial cells at a total weight of 10 to 50 g/L, an initial concentration of 2-carbonyl-4-(hydroxymethylphosphinyl)-butyric acid from 10 to 500 mM, glucose at a concentration of 12 to 750 mM, and ammonium sulfate at a concentration of 50 mM to 1.5 M.

6. The method of claim 4, wherein the reaction medium comprises the wet bacterial cells at a total weight of 15 g/L, an initial concentration of 2-carbonyl-4-(hydroxymethylphosphinyl)-butyric acid is 200 mM, glucose at a concentration of 250 mM, and ammonium sulfate at a concentration of 300 mM.

7. A method for constructing a cofactor self-sufficient *Escherichia coli*, comprising:
   (1) constructing one or more plasmids or expression vectors capable of intracellular linearization and self-recombination that comprise target genes including a NADH kinase gene, a glucose dehydrogenase gene, a glufosinate dehydrogenase gene and a gene of a NADP cofactor synthesis pathway, transforming the one or more plasmids or expression vectors comprising the target genes into *Escherichia coli* BL21 (DE3), and obtaining a transformed *Escherichia coli* with introduction of the one or more plasmids or expression vectors comprising the target genes that is a glufosinate dehydrogenase-glucose dehydrogenase-NADH kinase co-expressing gene engineering bacterium; wherein said NADH kinase gene sequence is as one of SEQ ID NOS: 1 to 5, said glucose dehydrogenase gene sequence is as shown in SEQ ID NO: 6, said glufosinate dehydrogenase gene sequence is as shown in SEQ ID NO: NO. 7, and said NADP cofactor synthesis pathway gene sequence is as shown in one of SEQ ID NO: 8 to 10; and
   (2) knocking out of any one or a combination of mazG, and nadR in the genome of the co-expressing gene-engineering bacterium to obtain said cofactor self-sufficient *Escherichia coli*.

8. The method as claimed in claim 7, wherein the sequence of said NADH kinase gene in step (1) is as shown in SEQ ID NO: 3 the gene sequence of said gene of NADP cofactor synthesis pathway is as shown in SEQ ID NO: 8; and the mazG and nadR genes are knocked out in step (2).

* * * * *